US011701267B2

(12) United States Patent
Greco et al.

(10) Patent No.: US 11,701,267 B2
(45) Date of Patent: Jul. 18, 2023

(54) GARMENTS WITH MOISTURE CAPTURE ASSEMBLIES AND ASSOCIATED METHODS

(71) Applicant: Knix Wear Inc., Toronto (CA)

(72) Inventors: Christina Greco, Toronto (CA); Talia Greenberg, Toronto (CA); Steven Hudson, Toronto (CA); Linda Kritikos, Toronto (CA); Julie Power, Toronto (CA)

(73) Assignee: Knix Wear Inc., Toronto (CA)

( * ) Notice: Subject to any disclaimer, the term of this patent is extended or adjusted under 35 U.S.C. 154(b) by 0 days.

(21) Appl. No.: 17/718,127

(22) Filed: Apr. 11, 2022

(65) Prior Publication Data
US 2023/0129586 A1    Apr. 27, 2023

Related U.S. Application Data

(60) Provisional application No. 63/271,637, filed on Oct. 25, 2021.

(51) Int. Cl.
*A61F 13/49*    (2006.01)
*A61F 13/15*    (2006.01)
*A41D 7/00*    (2006.01)

(52) U.S. Cl.
CPC .......... *A61F 13/15268* (2013.01); *A41D 7/00* (2013.01); *A61F 2013/15276* (2013.01); *A61F 2013/49088* (2013.01)

(58) Field of Classification Search
CPC .......... A61F 13/15268; A61F 13/49017; A61F 13/494; A61F 13/49406; A61F 13/4942;
(Continued)

(56) References Cited

U.S. PATENT DOCUMENTS 2,985,170 A    5/1961  Title
3,489,149 A *  1/1970  Larson .................... A61F 13/72
                                                    604/397
(Continued)

FOREIGN PATENT DOCUMENTS

AU    2006209375 A1    10/2006
AU    2014218471 B2    10/2016
(Continued)

OTHER PUBLICATIONS

English-language machine translation of Japan Patent Application Publication No. JP2005154922, Jun. 16, 2005.
(Continued)

*Primary Examiner* — Catharine L Anderson
*Assistant Examiner* — Lynne Anderson
(74) *Attorney, Agent, or Firm* — Kolitch Romano Dascenzo Gates LLC

(57) ABSTRACT

Garments comprise one or more bonds formed within a joined region of the garment; a garment base comprising at least one interior base layer and at least one exterior base layer; and a moisture capture assembly joined to the garment base within at least the joined region. The moisture capture assembly comprises a moisture retention portion configured to absorb and retain moisture from the wearer and an anti-leak portion configured to restrict moisture from exiting the moisture retention portion.

19 Claims, 14 Drawing Sheets

(58) Field of Classification Search
CPC .. A61F 2013/15276; A61F 2013/49088; A61F 2013/4948; A61F 2013/49493
See application file for complete search history.

(56) References Cited

U.S. PATENT DOCUMENTS

| | | | |
|---|---|---|---|
| 3,608,551 | A | 9/1971 | Saburo |
| 3,687,141 | A | 8/1972 | Matsuda |
| 4,044,769 | A | 8/1977 | Papajohn |
| 4,352,356 | A * | 10/1982 | Tong ................ A61F 13/74 604/397 |
| 4,355,425 | A | 10/1982 | Jones et al. |
| 4,560,381 | A | 12/1985 | Southwell |
| 4,781,962 | A | 11/1988 | Zamarripa et al. |
| 4,813,950 | A | 3/1989 | Branch |
| 4,847,134 | A | 7/1989 | Fahrenkrug et al. |
| 4,898,594 | A * | 2/1990 | Cottenden ......... A61F 13/491 604/397 |
| 5,151,092 | A | 9/1992 | Buell et al. |
| 5,167,897 | A | 12/1992 | Weber et al. |
| 5,217,782 | A | 6/1993 | Moretz et al. |
| 5,224,941 | A | 7/1993 | Simmons |
| 5,308,346 | A | 5/1994 | Sneller et al. |
| 5,342,338 | A | 8/1994 | Roe |
| 5,360,420 | A | 11/1994 | Cook et al. |
| 5,368,910 | A | 11/1994 | Langdon |
| 5,411,498 | A | 5/1995 | Fahrenkrug et al. |
| 5,449,352 | A | 9/1995 | Nishino et al. |
| 5,500,270 | A | 3/1996 | Langdon et al. |
| 5,507,895 | A | 4/1996 | Suekane |
| 5,518,801 | A | 5/1996 | Chappell et al. |
| 5,665,452 | A | 9/1997 | Langdon et al. |
| 5,677,028 | A | 10/1997 | Ravella |
| 5,693,169 | A | 12/1997 | Langdon et al. |
| H1732 | H | 6/1998 | Johnson |
| H1746 | H | 8/1998 | Carrier et al. |
| 5,851,204 | A | 12/1998 | Mizutani |
| 5,855,573 | A | 1/1999 | Johansson |
| 5,879,487 | A | 3/1999 | Ravella |
| 5,899,895 | A | 5/1999 | Robles et al. |
| 6,117,523 | A | 9/2000 | Sugahara |
| 6,120,487 | A | 9/2000 | Ashton |
| 6,149,497 | A | 11/2000 | Smith |
| 6,174,303 | B1 | 1/2001 | Suprise et al. |
| 6,192,521 | B1 | 2/2001 | Alberts et al. |
| 6,231,554 | B1 | 5/2001 | Menard |
| 6,240,569 | B1 | 6/2001 | Van Gompel et al. |
| 6,355,330 | B1 | 3/2002 | Koslow et al. |
| 6,381,994 | B1 | 5/2002 | Lee |
| 6,610,901 | B2 | 8/2003 | McMahon-Ayerst et al. |
| 6,622,312 | B2 | 9/2003 | Rabinowicz |
| 6,626,883 | B2 | 9/2003 | Wada et al. |
| 6,807,685 | B1 | 10/2004 | Hasegawa et al. |
| 6,861,520 | B1 | 3/2005 | Todd et al. |
| 7,008,887 | B2 | 3/2006 | Rearick et al. |
| 7,083,604 | B2 | 8/2006 | Sakaguchi |
| 7,156,828 | B2 | 1/2007 | Ostrow |
| RE39,919 | E | 11/2007 | Dodge, II et al. |
| 7,322,966 | B1 | 1/2008 | Deerin |
| 7,686,794 | B2 | 3/2010 | Mitchell |
| 7,951,128 | B1 | 5/2011 | Lewis |
| 8,058,343 | B2 | 11/2011 | Liu et al. |
| 8,117,675 | B2 | 2/2012 | Strange et al. |
| 8,282,618 | B2 | 10/2012 | Nordness et al. |
| 8,460,265 | B1 | 6/2013 | Calender |
| D701,018 | S | 3/2014 | Wexler |
| D716,020 | S | 10/2014 | Dunbar et al. |
| 8,935,813 | B2 | 1/2015 | O'Leary |
| 10,226,388 | B2 | 3/2019 | Nelson |
| 10,335,325 | B2 | 7/2019 | Sheldon et al. |
| 10,441,479 | B2 | 10/2019 | Griffiths |
| 10,441,480 | B2 | 10/2019 | Griffiths |
| 10,765,564 | B2 | 9/2020 | Lee et al. |
| 10,897,941 | B1 | 1/2021 | Smoter |
| 10,905,596 | B2 | 2/2021 | Sina et al. |
| 11,154,431 | B1 * | 10/2021 | Yip ................ A41B 17/00 |
| 11,207,225 | B2 | 12/2021 | Kajanthan et al. |
| 11,253,017 | B2 | 2/2022 | Friedrich |
| D948,167 | S | 4/2022 | Carpenter et al. |
| 11,331,229 | B2 | 5/2022 | Lee et al. |
| 11,395,774 | B2 | 7/2022 | Skinner et al. |
| 11,497,263 | B1 | 11/2022 | Deshaies et al. |
| 11,553,739 | B2 | 1/2023 | Henry |
| 2001/0031957 | A1 | 10/2001 | Prestley et al. |
| 2002/0177829 | A1 | 11/2002 | Fell et al. |
| 2003/0004488 | A1 | 1/2003 | Ashton et al. |
| 2003/0124927 | A1 | 7/2003 | Waldroup et al. |
| 2003/0143376 | A1 | 7/2003 | Toyoshima et al. |
| 2004/0229008 | A1 | 11/2004 | Hoying |
| 2004/0265533 | A1 | 12/2004 | Hoying et al. |
| 2005/0055002 | A1 | 3/2005 | Whitelaw et al. |
| 2005/0090790 | A1 | 4/2005 | Veith |
| 2005/0131365 | A1 | 6/2005 | Sakaguchi |
| 2006/0070163 | A1 | 4/2006 | Beck et al. |
| 2008/0108962 | A1 | 5/2008 | Furuta et al. |
| 2008/0110775 | A1 | 5/2008 | Beck et al. |
| 2008/0222781 | A1 | 9/2008 | Rhew |
| 2008/0275415 | A1 | 11/2008 | Wheeler et al. |
| 2008/0276352 | A1 | 11/2008 | Strange et al. |
| 2009/0240224 | A1 | 9/2009 | Underhill et al. |
| 2009/0247977 | A1 | 10/2009 | Takeuchi et al. |
| 2010/0222759 | A1 | 9/2010 | Hammons et al. |
| 2010/0249736 | A1 | 9/2010 | Png et al. |
| 2011/0048077 | A1 | 3/2011 | Warren et al. |
| 2011/0172621 | A1 | 7/2011 | Lee et al. |
| 2011/0224639 | A1 | 9/2011 | Venable |
| 2012/0123377 | A1 | 5/2012 | Back |
| 2013/0006209 | A1 | 1/2013 | Ruiz |
| 2013/0072888 | A1 | 3/2013 | Zorin |
| 2014/0039432 | A1 | 2/2014 | Dunbar et al. |
| 2014/0378935 | A1 | 12/2014 | Arayama et al. |
| 2016/0089276 | A1 | 3/2016 | Griffiths |
| 2016/0184146 | A1 | 6/2016 | Tulk et al. |
| 2019/0380886 | A1 | 12/2019 | Hammond |
| 2020/0000155 | A1 | 1/2020 | Etienne |
| 2020/0000649 | A1 | 1/2020 | Griffiths |
| 2020/0222256 | A1 | 7/2020 | Chong |
| 2021/0015684 | A1 | 1/2021 | Nakabugo |
| 2021/0030605 | A1 | 2/2021 | Kajanthan et al. |
| 2021/0282469 | A1 | 9/2021 | Siriwardena |
| 2021/0290447 | A1 | 9/2021 | Sepello et al. |
| 2021/0298369 | A1 | 9/2021 | Polstein et al. |
| 2022/0117790 | A1 | 4/2022 | Locke et al. |
| 2022/0117792 | A1 | 4/2022 | Bradford |
| 2022/0133544 | A1 | 5/2022 | Turton et al. |
| 2022/0354710 | A1 | 11/2022 | Sepello et al. |
| 2022/0408848 | A1 | 12/2022 | Krupa |
| 2023/0010999 | A1 | 1/2023 | Sieck et al. |

FOREIGN PATENT DOCUMENTS

| | | |
|---|---|---|
| CA | 2126280 | 12/1994 |
| CA | 2126281 | 12/1994 |
| CA | 2152135 | 12/1995 |
| EP | 1370161 | 5/2006 |
| JP | 2005154922 | 6/2005 |
| JP | 2005154924 | 6/2005 |
| KR | 20070018490 | 2/2007 |
| KR | 100694187 | 3/2007 |
| WO | WO 1997046198 | 12/1997 |
| WO | WO 2006036841 | 4/2006 |

OTHER PUBLICATIONS

English-language machine translation of Japan Patent Application Publication No. JP2005154924, Jun. 16, 2005.

English-language machine translation of Korea Patent No. KR100694187, Mar. 6, 2007.

English-language machine translation of Korea Patent Application Publication No. KR20070018490, Feb. 14, 2007.

"Bemis SewFree" webpage (www.bemisheatseal.com/Sewfree.htm), 2 pages, available at least as early as Aug. 4, 2001, retrieved

(56) References Cited

OTHER PUBLICATIONS from Internet Archive Wayback Machine (https://web.archive.org/web/20010804041402/http://www.bemisheatseal.com:%2080/Sewfree.htm) on Jan. 29, 2021.
Lo, T.Y., "Techtextil/Avantex 2005 (2)" *Textile Asia*, 2005, pp. 26-27.
Isaacs, Mac, "Seamless: Eliminating Stitches—More Than a Buzzword," *AATCC Review*, Nov. 2005, pp. 16-19.
Swantko, Kathlyn, "Forming a New Bond,"*FabricTrends: A GearTrends Supplement*, 2004, pp. 12-14.
Bemis Associates, *Sewfree Adhesive Films for Intimate Apparel*, 2013, 8 pages.
Photographs of Adidas Techfit Period-Proof Biker Short Tights, ordered Jun. 24, 2021.
Photographs Lilova Seamless High Waist, ordered Oct. 12, 2021.
Photographs Lilova Swimwear One-Piece Classic, ordered Oct. 12, 2021.
Photographs of Modibodi Seamfree Bikini Moderate-Heavy, ordered Feb. 9, 2022.
Photographs of Proof Leakproof Hipster Underwear, ordered Aug. 7, 2020.
Photographs of Pure Rosy Banded Brief—Jam, ordered Oct. 12, 2021.
Photographs of Ruby /Love Period Underwear Bikini—Pretty in Pink, ordered May 6, 2021.
Photographs of SPEAX by Thinx Hiphugger Women's Underwear—Leakproof, Breathable—M—Beige, ordered Feb. 7, 2020.
Photographs of TomboyX Leakproof Bikini—Plum, ordered Nov. 10, 2020.

\* cited by examiner

GARMENTS WITH MOISTURE CAPTURE ASSEMBLIES AND ASSOCIATED METHODS

RELATED APPLICATION

This application claims benefit of U.S. Provisional Patent Application No. 63/271,637, filed on Oct. 25, 2021, the complete disclosure of which is incorporated herein by reference.

FIELD

The present disclosure relates to garments with moisture capture assemblies and associated methods.

BACKGROUND

Garments and other wearable accessories that are configured to be worn adjacent to a wearer's crotch often exhibit moisture-absorbing properties, such as to absorb and/or retain menstrual fluids and/or urine produced by the wearer. In particular, it generally is desirable that such garments absorb and retain such fluids in a discreet and leak-proof manner, such as to hide such fluids from view and/or to enhance the wearer's comfort. In the field of undergarments, various solutions exist for configuring undergarments to absorb and retain fluids. However, in the case of garments in the form of swimwear, special considerations must be taken into account to ensure that such fluids remain retained within the garment while swimming, and to ensure that the water in which the wearer is swimming does not penetrate and/or saturate the garment.

SUMMARY

Garments with moisture capture assemblies and associated methods are disclosed herein. A garment configured to be worn by a wearer includes a crotch region, a joined region, a garment base, and a moisture capture assembly joined to the garment base within the joined region. Specifically, the moisture capture assembly is positioned at least partially within the crotch region. The moisture capture assembly includes an assembly interior side that faces the wearer when the garment is worn by the wearer and an assembly exterior side that faces away from the wearer when the garment is worn by the wearer. The moisture capture assembly further includes a moisture retention portion configured to absorb and retain moisture from the wearer and an anti-leak portion configured to restrict moisture from exiting the moisture retention portion. The moisture capture assembly is joined to the garment base via bonds formed within the joined region. In some examples, the garment is an article of swimwear.

DESCRIPTION

Figure 1:
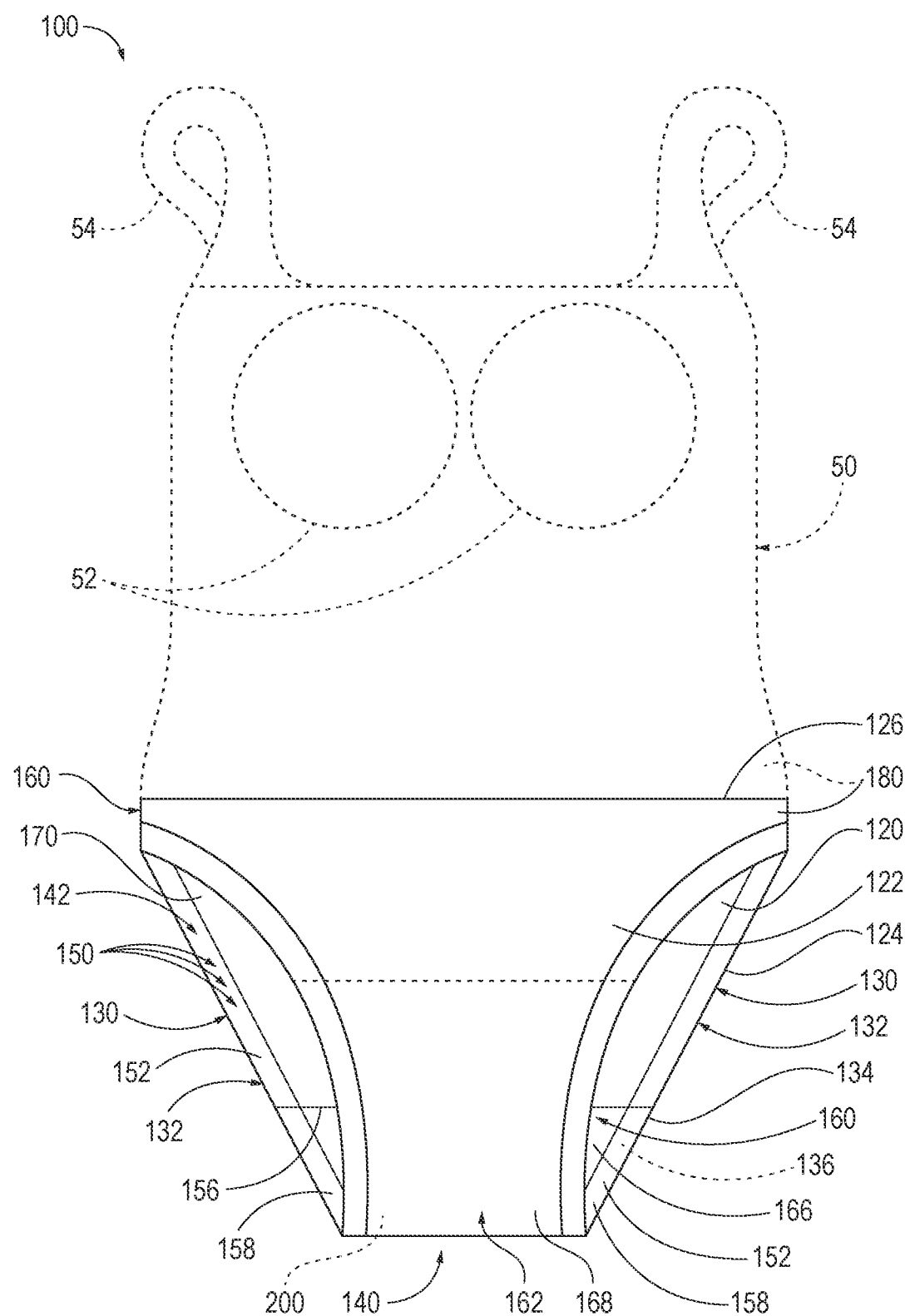
FIG. 1 is a schematic front view illustrating examples of garments according to the present disclosure.

FIGS. 1-14 provide examples of garments 100 including moisture capture assemblies 200 and/or of methods 300 of manufacturing garments 100, according to the present disclosure. Elements that serve a similar, or at least substantially similar, purpose are labeled with like numbers in each of FIGS. 1-14, and these elements may not be discussed in detail herein with reference to each of FIGS. 1-14. Similarly, all elements may not be labeled in each of FIGS. 1-14, but reference numerals associated therewith may be utilized herein for consistency. Elements, components, and/or features that are discussed herein with reference to one or more of FIGS. 1-14 may be included in and/or utilized with any of FIGS. 1-14 without departing from the scope of the present disclosure. In general, elements that are likely to be included in a particular embodiment or example are illustrated in solid lines, while elements that are optional are illustrated in dashed lines. However, elements that are shown in solid lines may not be essential and, in some embodiments or examples, may be omitted without departing from the scope of the present disclosure.

Figure 2:
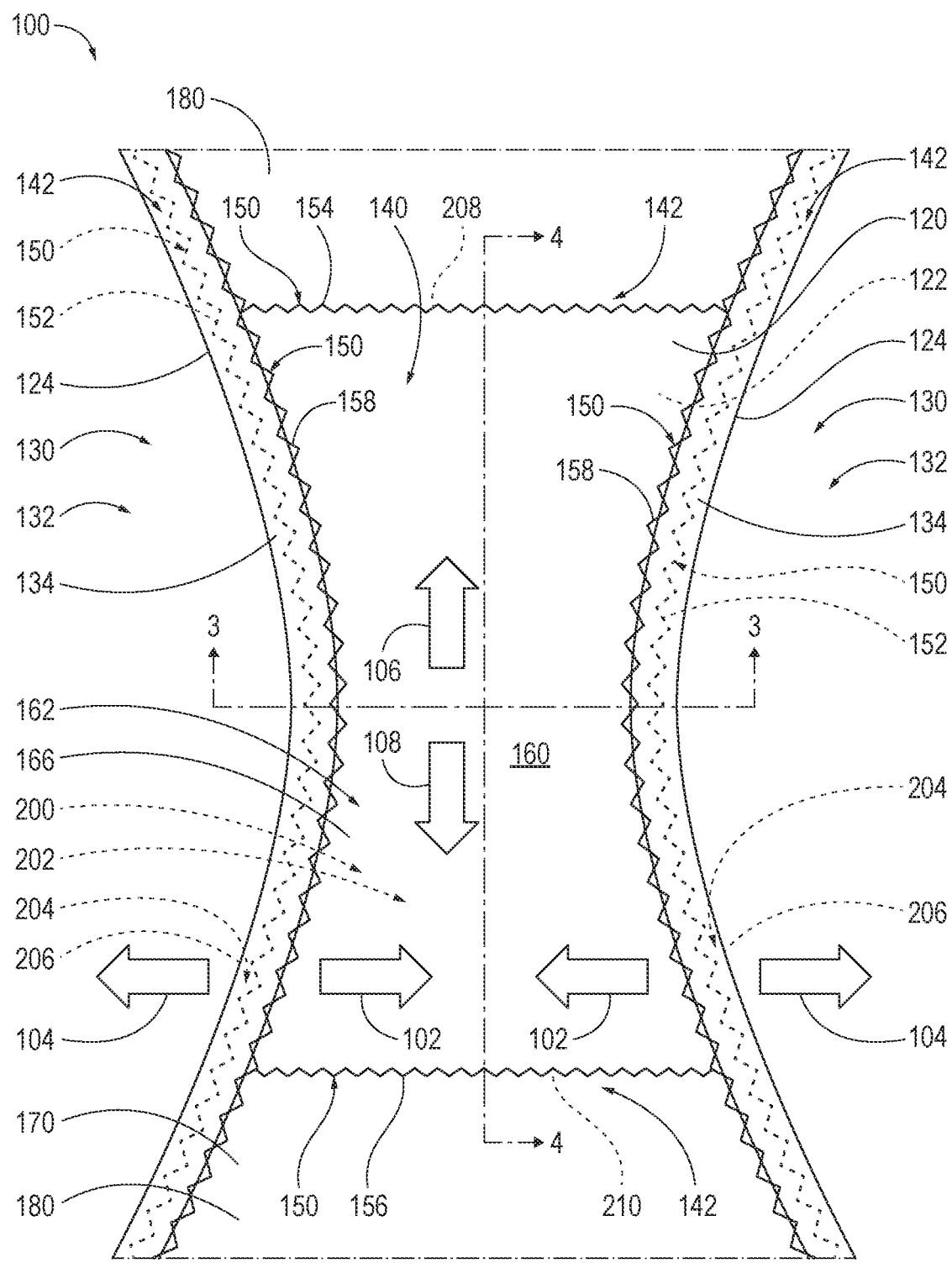
FIG. 2 is a schematic fragmentary top view illustrating examples of crotch regions of garments according to the present disclosure.
Figure 3:
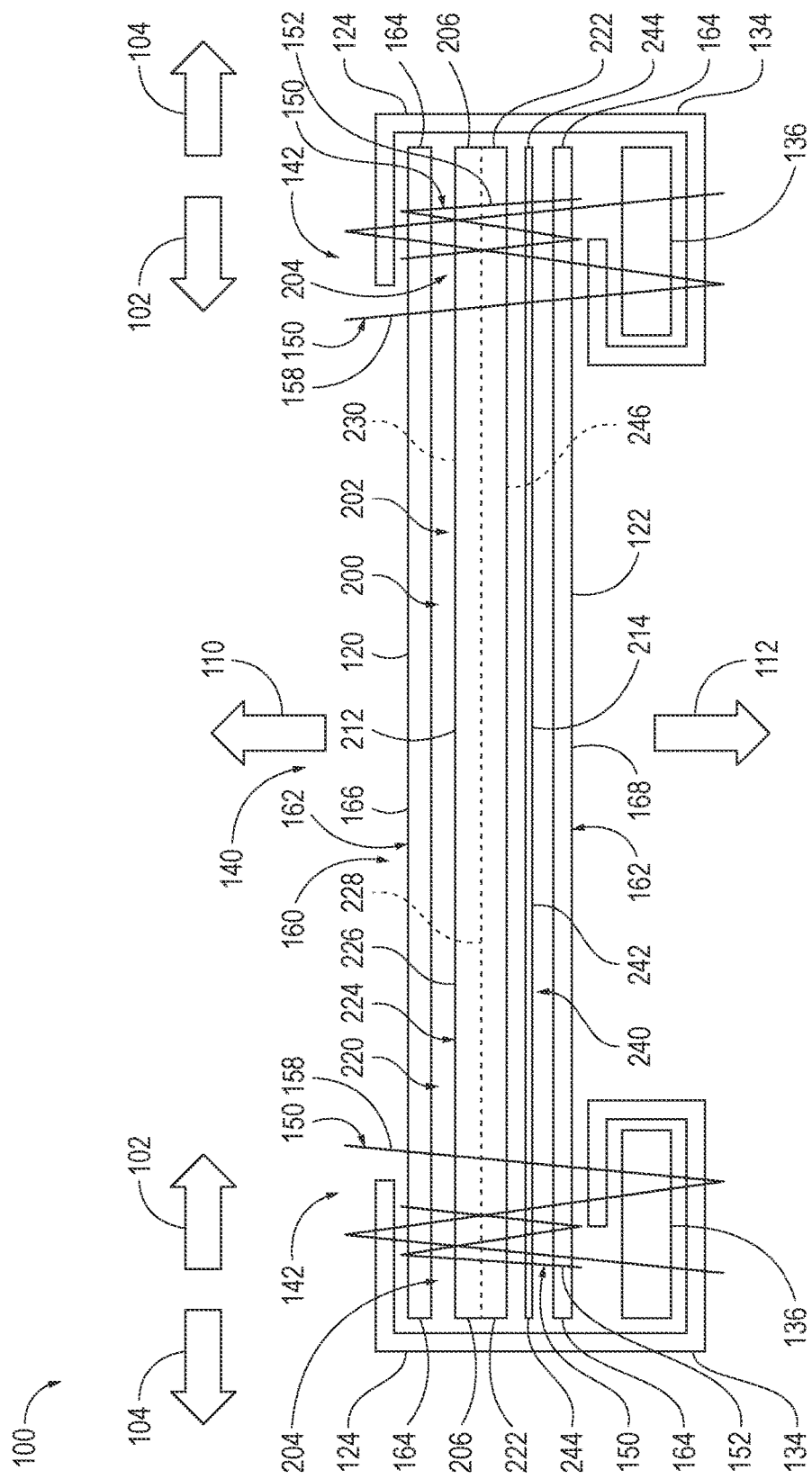
FIG. 3 is a schematic cross-sectional view as viewed along line 3-3 of FIG. 2 illustrating examples of garments according to the present disclosure.
Figure 4:
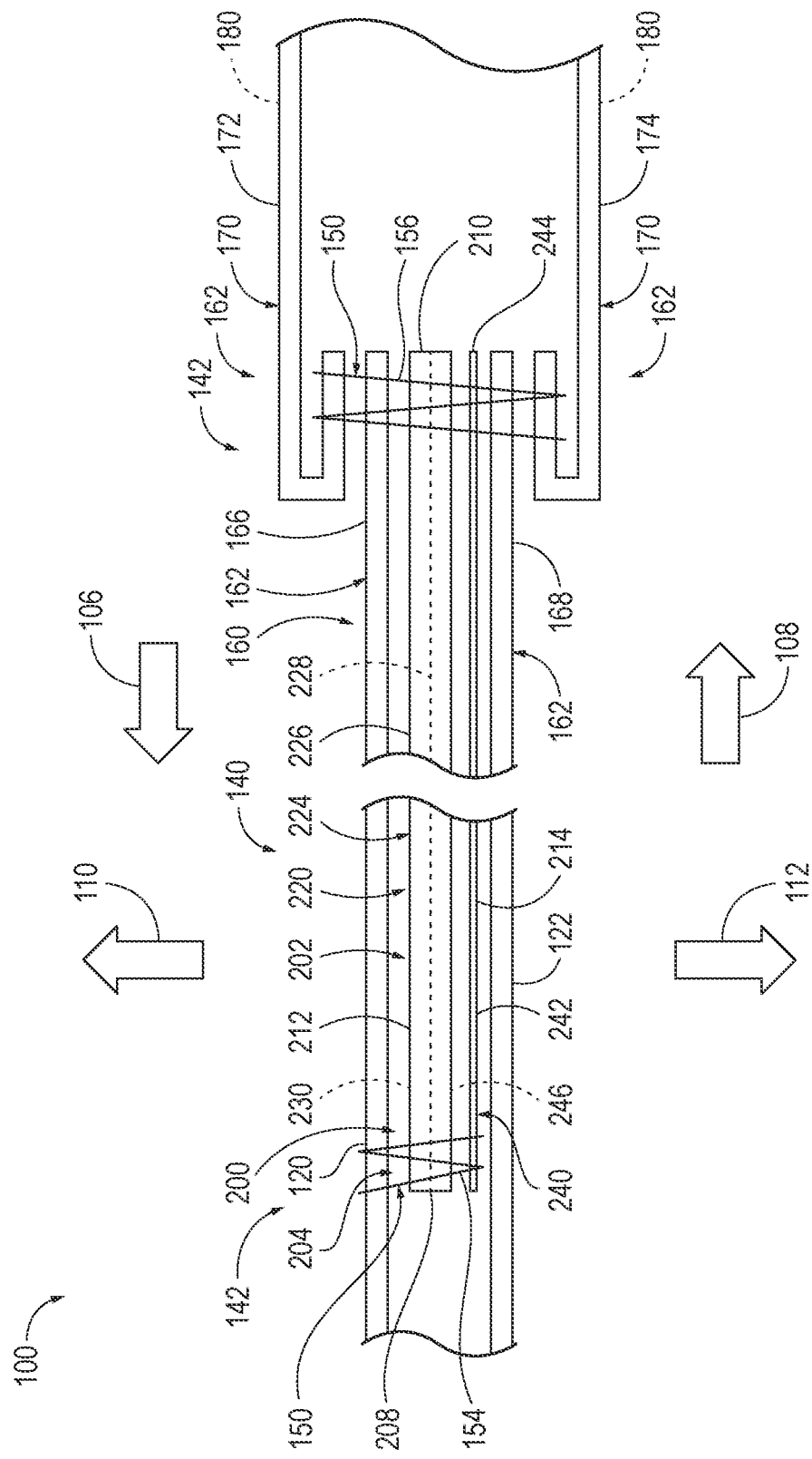
FIG. 4 is a schematic fragmentary cross-sectional view as viewed along line 4-4 of FIG. 2 illustrating examples of garments according to the present disclosure.
Figure 5:
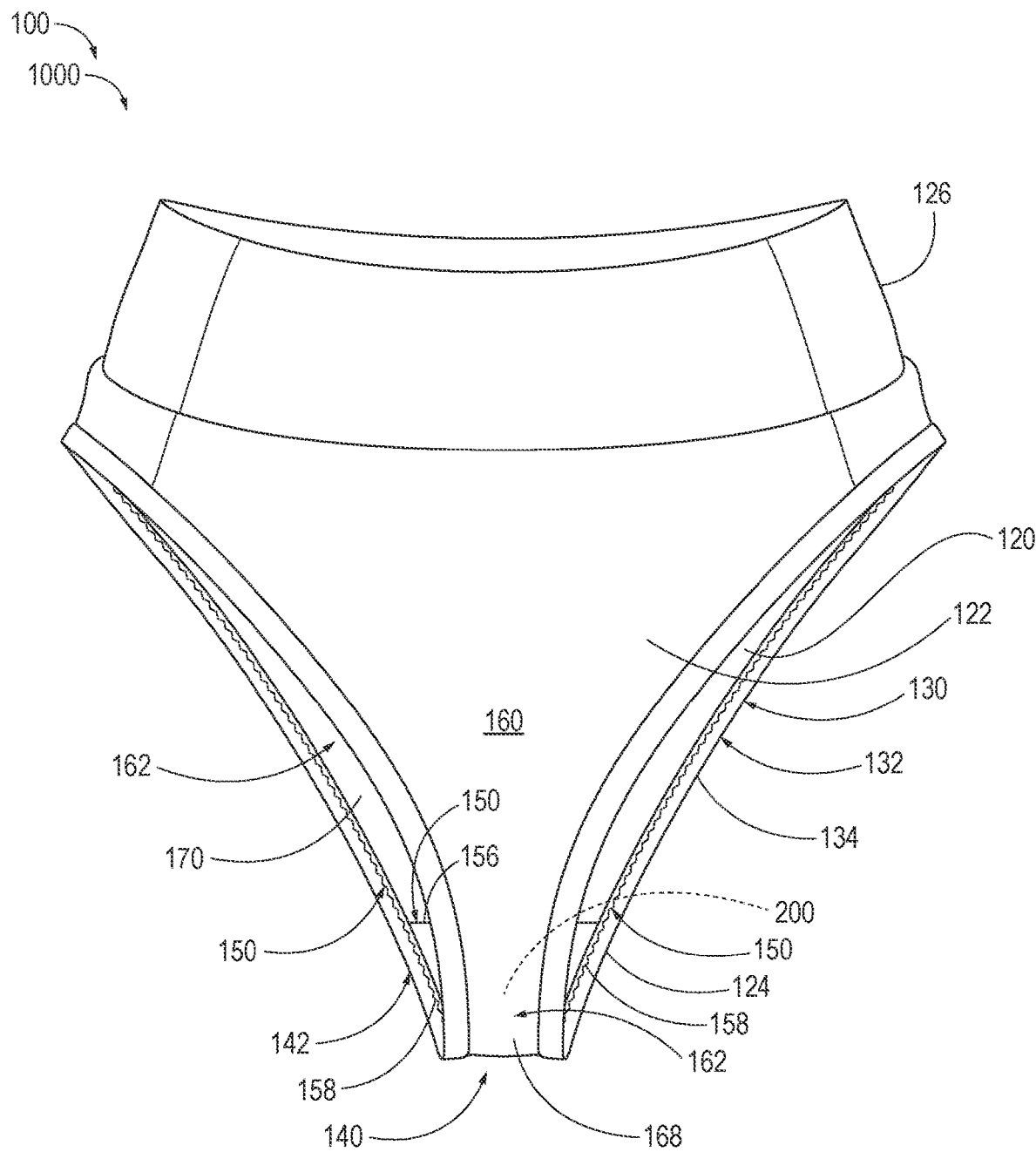
FIG. 5 is a front view illustrating a first example garment according to the present disclosure.
Figure 6:
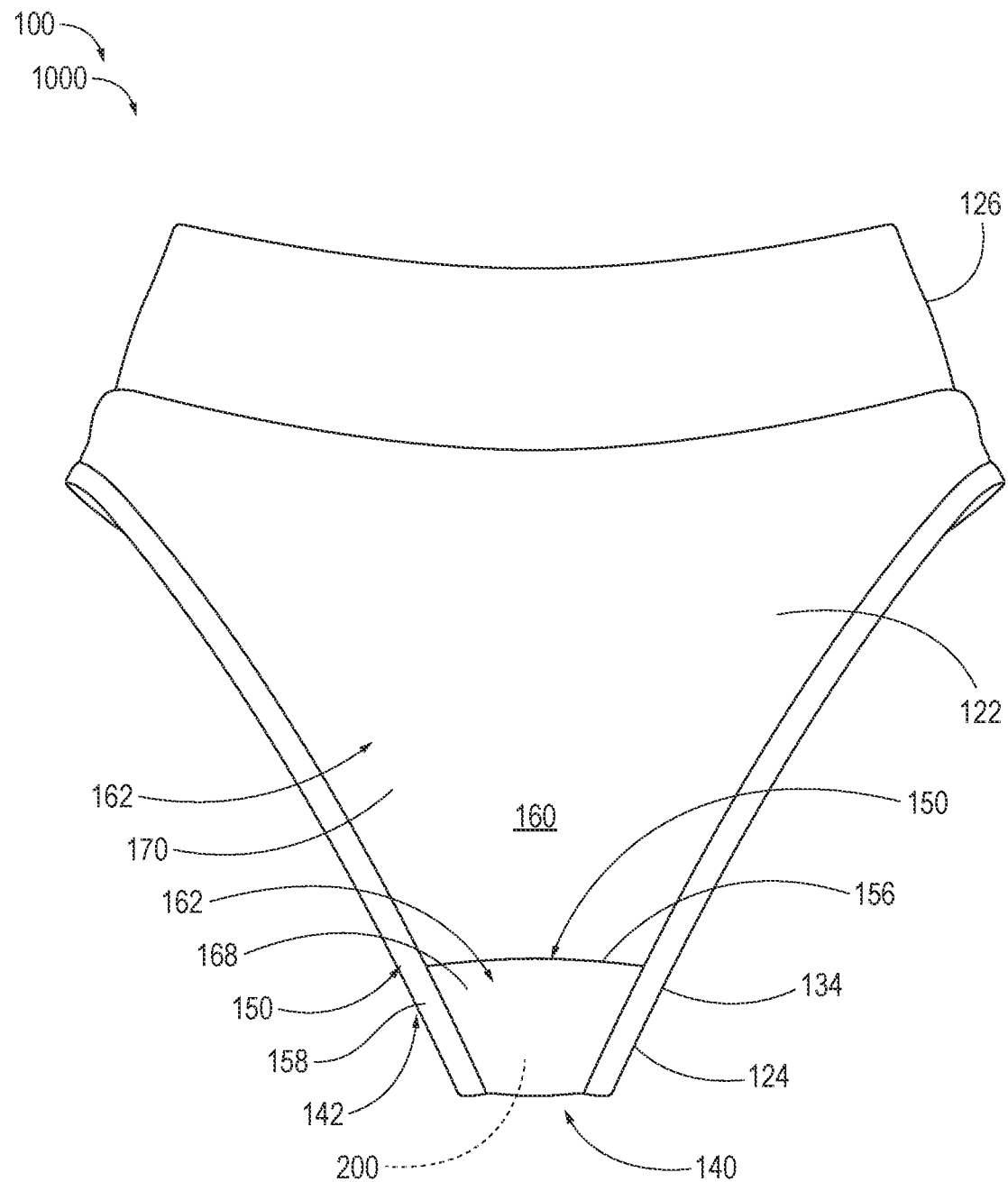
FIG. 6 is a rear view illustrating the first example garment of FIG. 5.
Figure 7:
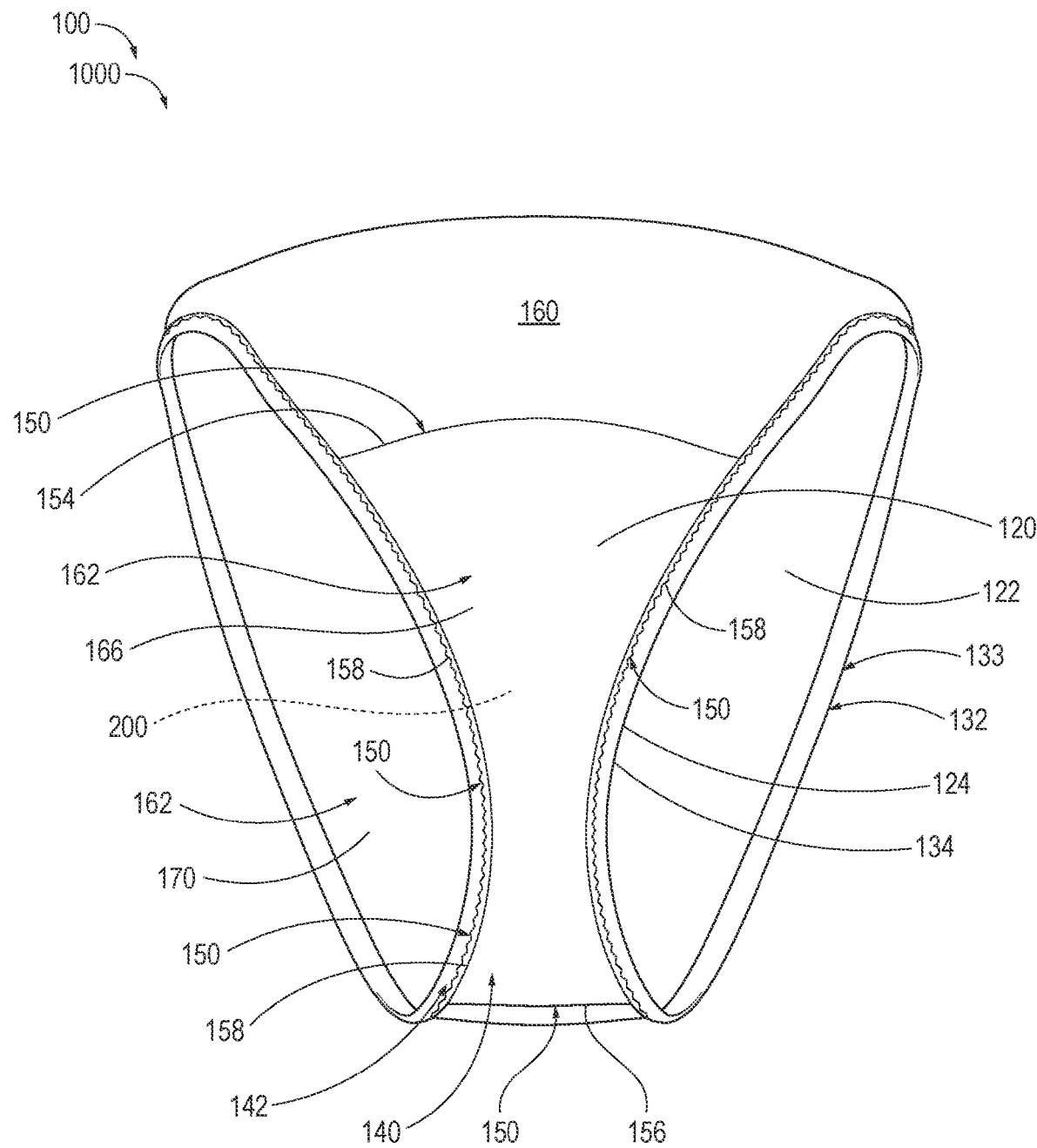
FIG. 7 is a top view illustrating a crotch region, according to the present disclosure, of the first example garment of FIG. 5.
Figure 8:
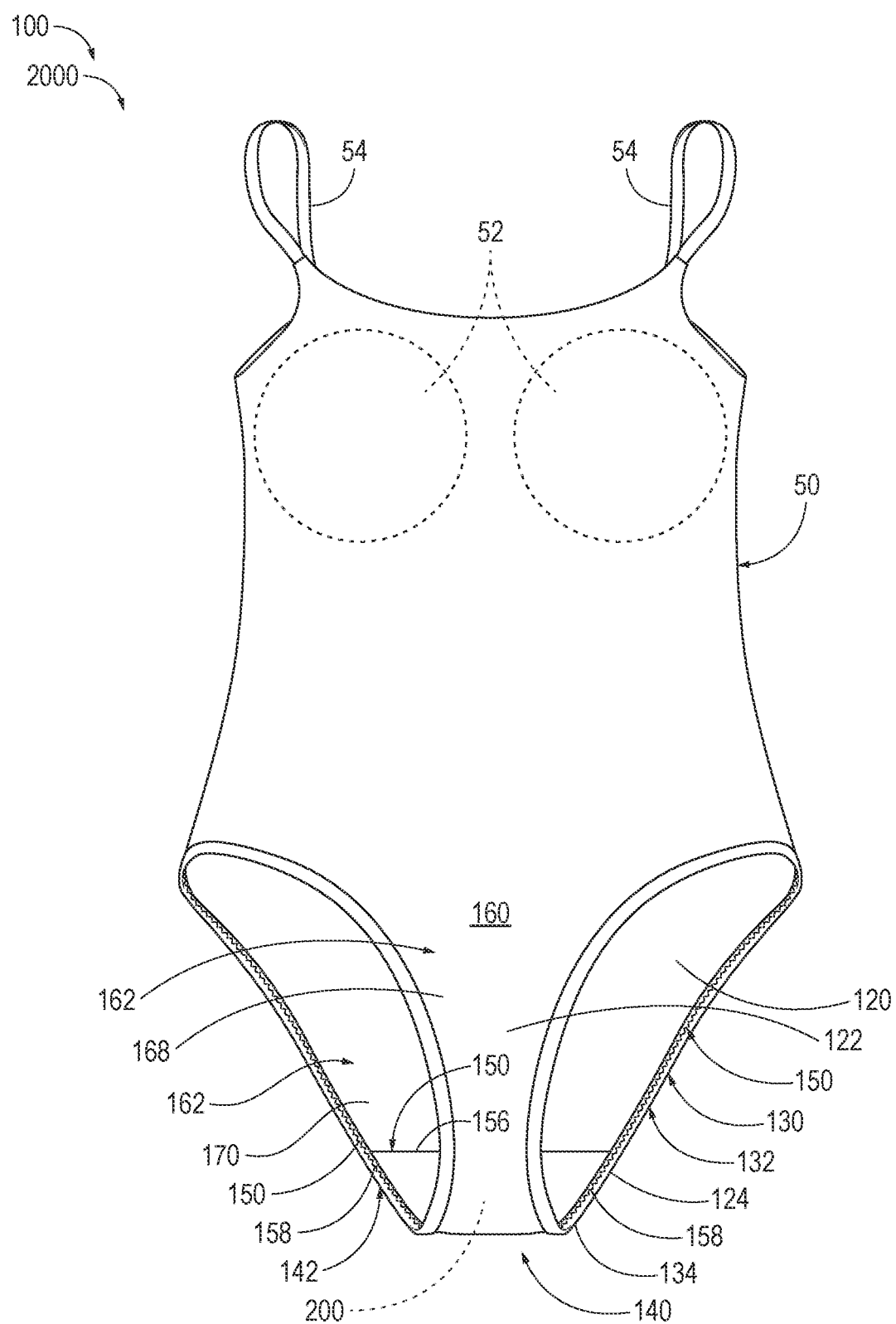
FIG. 8 is a front view illustrating a second example garment according to the present disclosure.
Figure 9:
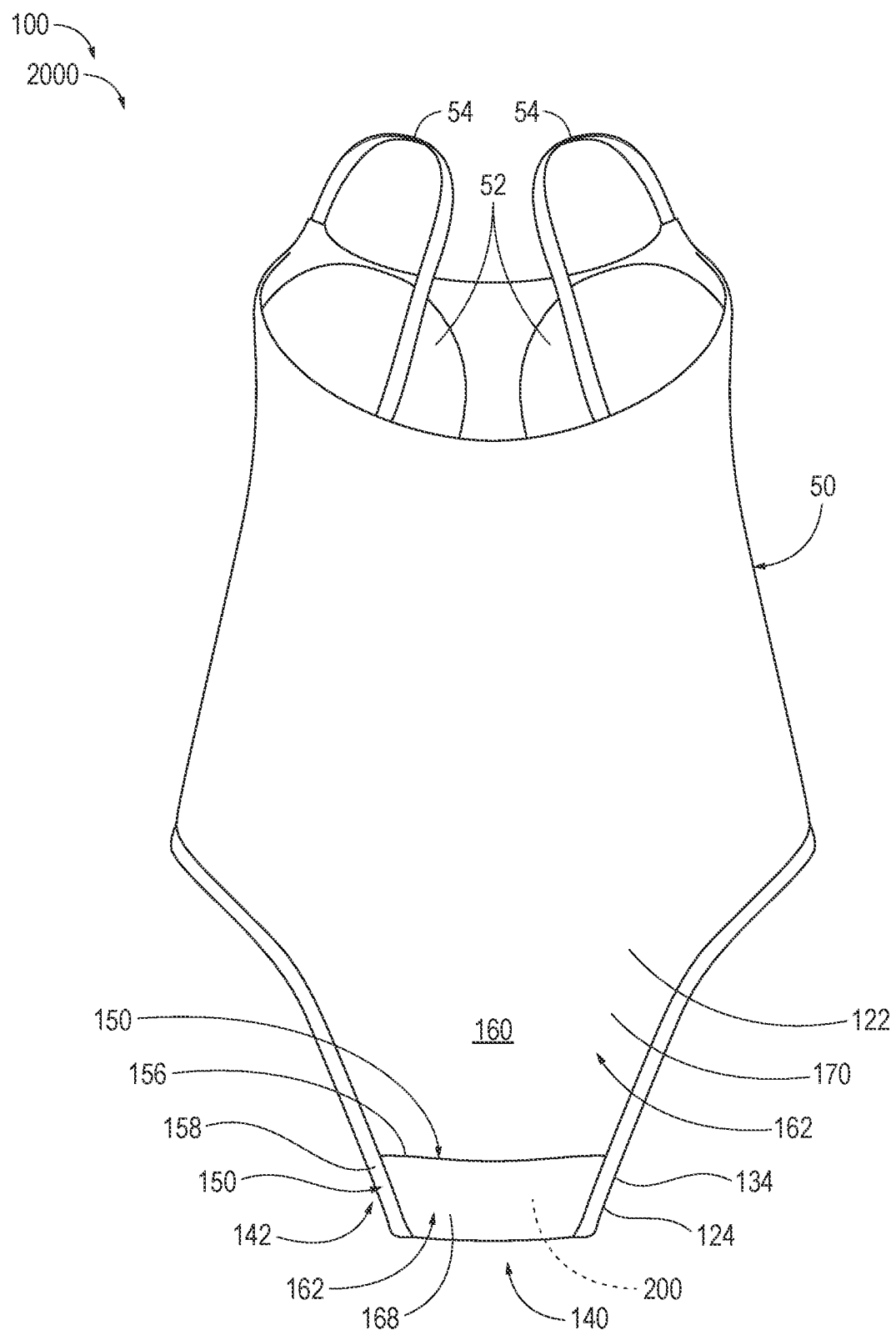
FIG. 9 is a rear view illustrating the second example garment of FIG. 8.
Figure 10:
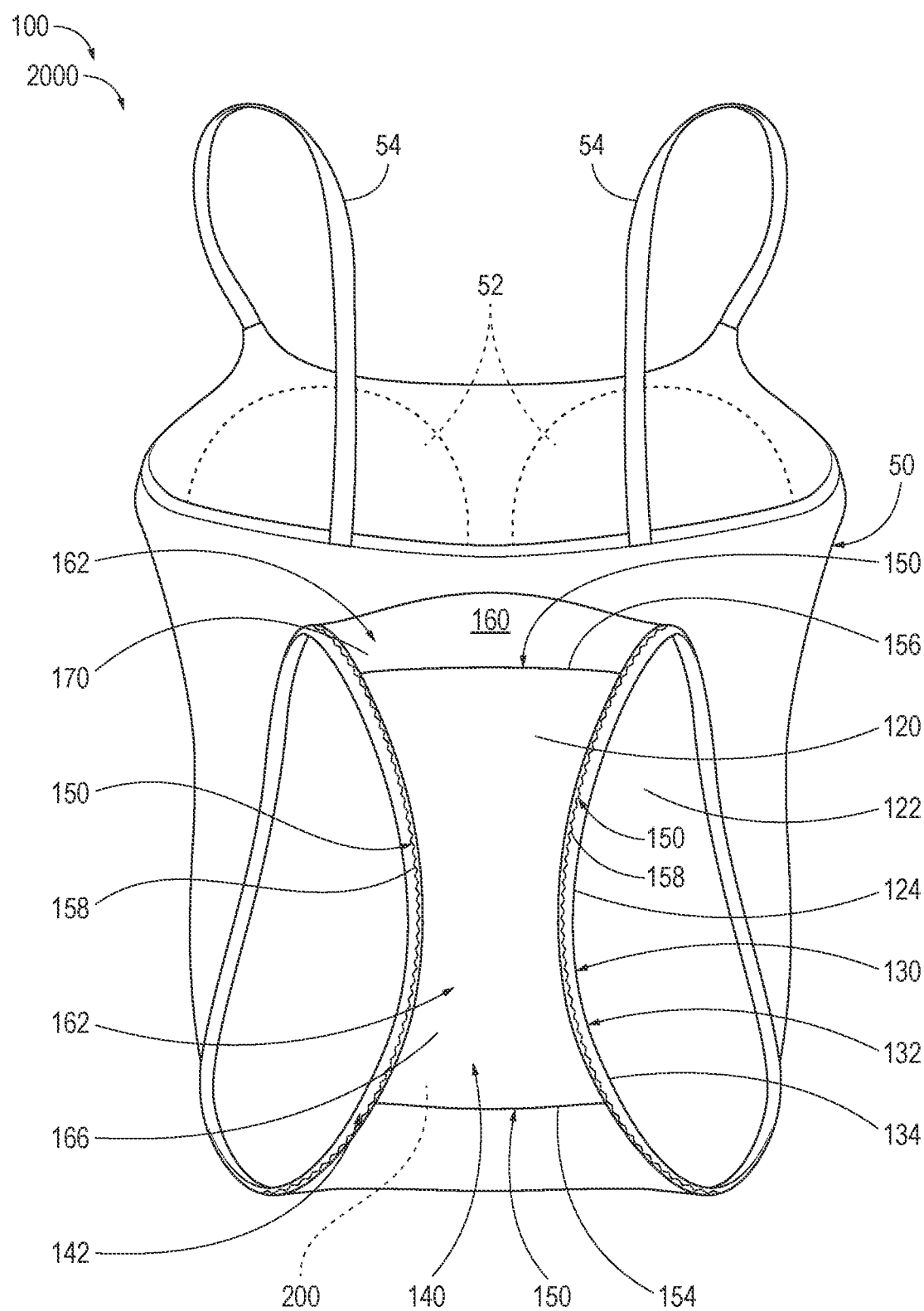
FIG. 10 is a view illustrating the crotch region from the top of the second example garment of FIG. 8.
Figure 11:
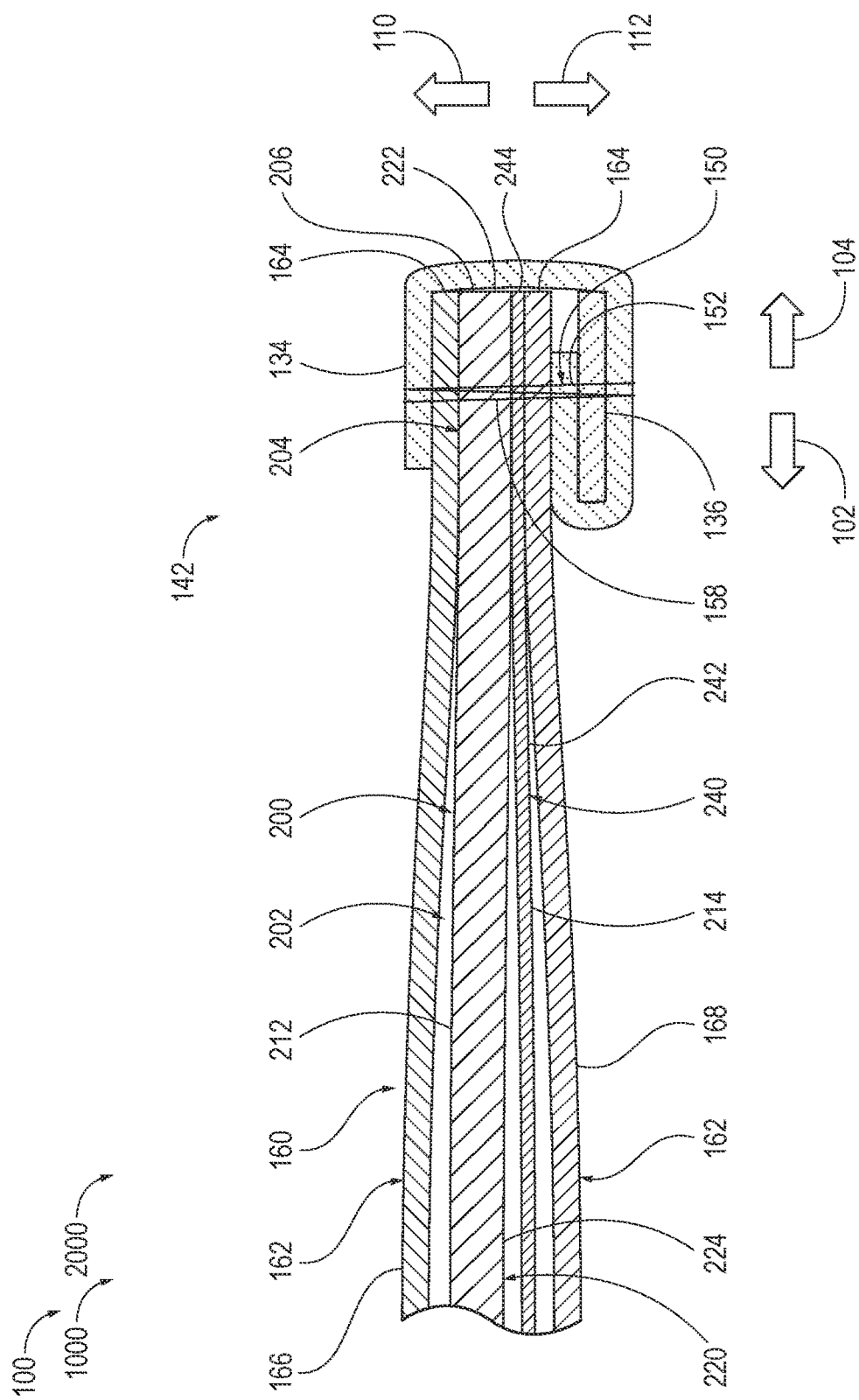
FIG. 11 is a fragmentary cross-sectional view illustrating an example of a garment lateral edge of a garment according to the present disclosure.
Figure 12:
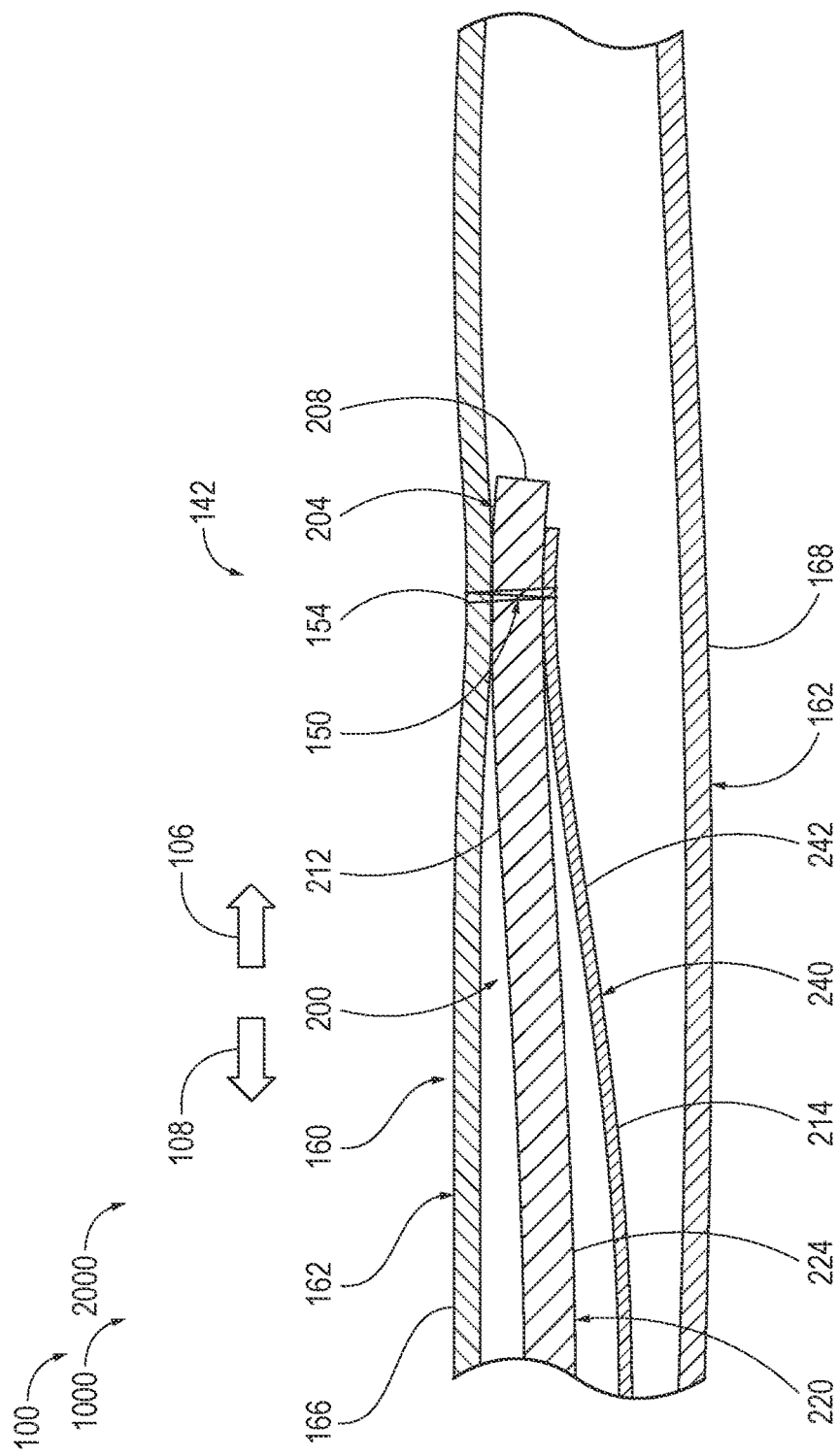
FIG. 12 is a fragmentary cross-sectional view illustrating an example of an anterior region stitching seam according to the present disclosure.
Figure 13:
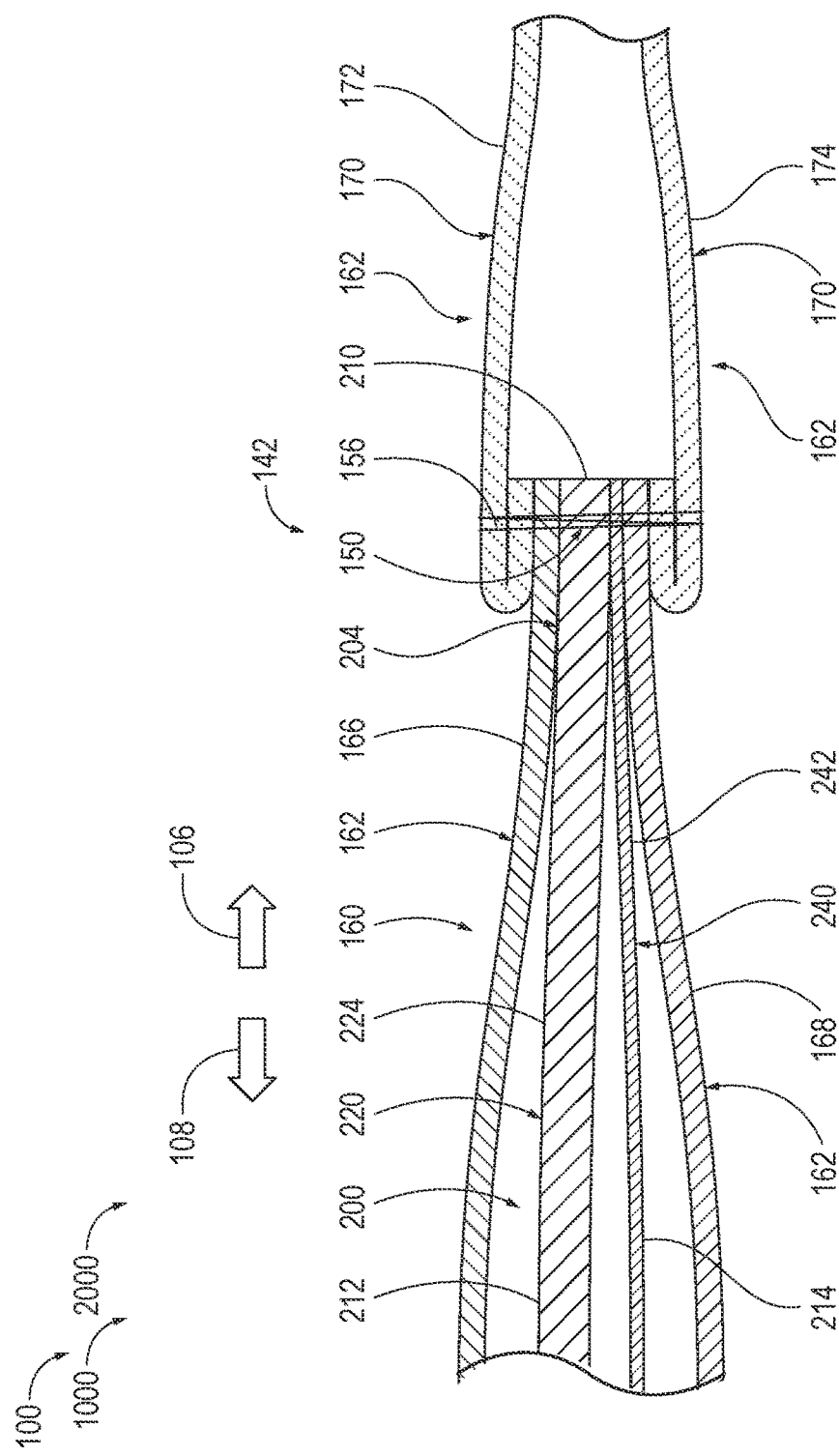
FIG. 13 is a fragmentary cross-sectional view illustrating an example of a posterior region stitching seam according to the present disclosure.

FIG. 1 is a schematic front view illustrating examples of garments 100 according to the present disclosure, while FIG. 2 is a schematic fragmentary top view illustrating examples of crotch regions 140 of garments 100. FIGS. 3-4 are schematic cross-sectional front and side views, respectively, as viewed along the lines 3-3 and 4-4 on FIG. 2, respectively. FIGS. 5-7 illustrate a first example garment 1000, which is an example of garment 100, while FIGS. 8-10 illustrate a second example garment 2000, which is another example of garment 100. FIGS. 11-13 are fragmentary cross-sectional views illustrating aspects of examples of garments 100, such as aspects of first example garment 1000 and/or of second example garment 2000, as described in more detail herein.

As schematically illustrated in FIGS. 1-4 and less schematically illustrated in FIGS. 5-10, a garment 100 configured to be worn by a wearer includes a garment base 160, a moisture capture assembly 200, and a joined region 142 such that the moisture capture assembly is joined to the garment base within at least the joined region. As schematically illustrated in FIGS. 1-4, and as described in more detail herein, moisture capture assembly 200 is joined to garment base 160 via one or more bonds 150 formed within joined region 142. That is, as used herein, joined region 142 generally refers to a region, or collection of regions, in which bonds 150 are formed. Joined region 142 thus may include one or more connected and/or spaced-apart elongate regions of garment 100. In this manner, bonds 150 collectively may define joined region 142. As a more specific example, and with reference to FIG. 2, moisture capture assembly 200 may be described as including a moisture capture assembly central region 202 and a moisture capture assembly peripheral region 204 that circumferentially encloses the moisture capture assembly central region, such that joined region 142 includes at least a portion of the moisture capture assembly peripheral region. In particular, in some examples, and as schematically illustrated in FIG. 2, joined region 142 extends at least substantially around a perimeter of moisture capture assembly peripheral region 204.

Bonds 150 may be created utilizing any suitable technique, including stitching, adhesive, thermo-compression, etc. That is, a bond 150 may be described as a stitching seam in some examples and may be described as an adhesive bond in other examples. As used herein, the term "stitching seam" is intended to refer to any suitable line, row, series, and/or other form of stitching that binds and/or joins two or more elements of garment 100 to one another. Stitching seams according to the present disclosure generally include and/or consist of a stitching thread that is sewn through the elements of garment 100 to be joined in any suitable pattern. Any stitching seam according to the present disclosure may utilize and/or embody any suitable sewing technique and/or pattern, examples of which include a lapped seam, a superimposed seam, a bound seam, a flat seam, a lockstitch, a chainstitch, a covering stitch, etc. Throughout the drawings, bonds 150 generally are schematically represented as stitching seams 150; however, the representation thereof in the drawings does not represent a specific type or technique of stitch or seam and does not limit garments 100 to including stitching seams. That is, each schematically represented stitching seam should be understood to also schematically and optionally represent an adhesive bond.

As schematically illustrated in FIGS. 3-4 and less schematically illustrated in FIGS. 11-13, moisture capture assembly 200 includes an assembly interior side 212 that faces the wearer when the garment is worn by the wearer and an assembly exterior side 214 that faces away from the wearer when the garment is worn by the wearer. As additionally schematically illustrated in FIGS. 3-4 and less schematically illustrated in FIGS. 11-13, moisture capture assembly 200 further includes a moisture retention portion 220 configured to absorb and retain moisture from the wearer, as well as an anti-leak portion 240 configured to restrict moisture from exiting the moisture retention portion. In the present disclosure, moisture retention portion 220 also may be referred to as a moisture retention subassembly 220, and/or anti-leak portion 240 may be referred to as an anti-leak subassembly 240.

Moisture capture assembly 200 may be positioned within any suitable region of garment 100. In particular, in some examples, and as schematically illustrated in FIGS. 1-4 and less schematically illustrated in FIGS. 5-10, garment 100 includes a crotch region 140 that is configured to be positioned adjacent to the wearer's crotch and/or groin area when garment 100 is worn by the wearer, and moisture capture assembly 200 is positioned at least partially within the crotch region. Additionally or alternatively, and as described in more detail herein, garment base 160 may support moisture capture assembly 200, such as within crotch region 140. In some examples, and as schematically illustrated in FIGS. 1-4 and less schematically illustrated in FIGS. 5-10, garment 100 includes a garment interior surface 120 that faces the wearer when the garment is worn by the wearer and a garment exterior surface 122 that faces away from the wearer when the garment is worn by the wearer.

Garment 100 may include and/or be any of a variety of garments and/or worn accessories. In particular, the present disclosure generally relates to examples in which garment 100 is an article of swimwear, such as a swimsuit, a one-piece swimsuit, a swimsuit bottom, and/or a bikini bottom. Additionally or alternatively, and as schematically illustrated in FIG. 1, garment 100 may include a torso region 50 configured to overlie at least a portion of the wearer's torso when the wearer wears the garment. In some examples, and as additionally schematically illustrated in FIG. 1, garment 100 and/or torso region 50 includes one or more breast cups 52 configured to overlie and/or support the wearer's breasts when the wearer wears the garment and/or one or more shoulder straps 54 configured to be worn over the wearer's shoulders when the wearer wears the garment. However, such examples are not limiting, and it additionally is within the scope of the present disclosure that garment 100 may include, be, and/or be included in any other suitable garment, examples of which include an undergarment, a short (e.g., a pair of shorts), a menstrual pad, an outerwear garment, an activewear garment, etc. In various examples according to the present disclosure, garment 100 is configured to be washed and re-worn numerous times. In this manner, in such examples, garment 100 is distinct from a disposable absorbent garment that is configured to be worn only once, or only a small number of times, before being disposed and replaced.

The present disclosure generally relates to examples in which moisture capture assembly 200 is positioned at least partially within crotch region 140. However, such examples are not limiting, and it is to be understood that the various aspects, features, constructions, etc. of garments 100 according to the present disclosure may be applied to any of a variety of articles, including garments 100 that are not configured to be worn adjacent to a wearer's groin area and/or garments that do not include crotch region 140. As examples, aspects of garments 100 according to the present disclosure, such as moisture capture assembly 200 and/or bonds 150, may be configured to absorb sweat associated with the user's arm pits, may be configured to restrict moisture from penetrating an outer garment to reach the user's skin, etc.

Garment 100 may be configured to absorb and retain any of a variety of fluids, such as may be associated with and/or produced by the wearer while the wearer wears the garment. For example, garment 100 and/or moisture capture assembly 200 thereof may be configured to absorb and retain blood and/or other menstrual fluids produced by the wearer, and/or to absorb and retain urine produced by the wearer, such as may be associated with an incontinence condition. However, in some examples, such as when garment 100 is an article of swimwear, it may be desirable to configure moisture capture assembly 200 specifically to restrict the retained fluids from leaking into an external environment, such as a body of water in which the garment is worn. Similarly, when garment 100 is an article of swimwear, it may be desirable to configure moisture capture assembly 200 to restrict water from the external environment from leaking into and/or saturating moisture capture assembly 200. Accordingly, garments 100 according to the present disclosure generally are configured to isolate moisture retention portion 220 from the external environment, such as with anti-leak portion 240, while additionally supporting moisture retention portion 220 within garment base 160 in a manner that at least partially conceals the presence of the moisture capture assembly. In this manner, garments 100 according to the present disclosure may offer the wearer protection against leakage of bodily fluids away from the garment while maintaining the external appearance of a conventional garment.

As described in more detail herein, various components and/or features of garment 100 may be described with reference to directions defined relative to the garment. For example, and as schematically illustrated in FIGS. 2-4, garment 100 and/or a portion thereof may be described as defining a laterally inward direction 102 and a laterally outward direction 104 (shown in FIGS. 2-3), such that laterally inward direction 102 generally is directed toward a central region of garment 100 and/or of crotch region 140, and such that laterally outward direction 104 is opposite the laterally inward direction. For example, and as schematically illustrated in FIGS. 2-3, garment 100 may include a pair of garment lateral edges 124 in a region proximal to moisture capture assembly 200, and laterally inward direction 102 may be directed from each garment lateral edge 124 toward moisture capture assembly central region 202. In such examples, at least a portion of moisture capture assembly 200 may be described as extending away from each garment lateral edge 124 along laterally inward direction 102.

As schematically illustrated at least in FIG. 3, moisture capture assembly 200 may be described as extending between and terminating at a pair of moisture capture assembly lateral edges 206. In such examples, moisture capture assembly peripheral region 204 may be described as including each moisture capture assembly lateral edge 206. Additionally, and as further schematically illustrated in FIG. 3, moisture retention portion 220 of moisture capture assembly 200 may be described as extending between and terminating at a pair of moisture retention portion lateral edges 222. In some examples, each moisture retention portion lateral edge 222 defines and/or is a respective moisture capture assembly lateral edge 206 of moisture capture assembly 200. Stated differently, in such examples, no portion of moisture capture assembly 200 extends further along laterally outward direction 104 than moisture retention portion 220. Alternatively, in some other examples, each moisture capture assembly lateral edge 206 is spaced apart from the respective moisture retention portion lateral edge 222 along laterally outward direction 104.

Additionally, and as schematically illustrated in FIGS. 2 and 4, garment 100 and/or a portion thereof may be described as defining a laterally anterior direction 106 and a laterally posterior direction 108 that is opposite the laterally anterior direction. In particular, laterally anterior direction 106 may correspond to a direction that is parallel to a surface of garment 100 and that is directed toward an anterior and/or forward portion of garment 100, while laterally posterior direction 108 may correspond to a direction that is parallel to a surface of garment 100 and that is directed toward a posterior and/or rearward portion of garment 100. As schematically illustrated in FIGS. 2 and 4, moisture capture assembly 200 may be described as extending between and terminating at a moisture capture assembly anterior edge 208 and a moisture capture assembly posterior edge 210, with the moisture capture assembly anterior edge being spaced apart from the moisture capture assembly posterior edge along the laterally anterior direction.

Additionally, and as schematically illustrated in FIGS. 3-4, garment 100 may be described as defining a transversely inward direction 110 that is directed toward the wearer when garment 100 is worn by the wearer and a transversely outward direction 112 that is opposite the transversely inward direction. In this manner, each of transversely inward direction 110 and transversely outward direction 112 is perpendicular to each of laterally inward direction 102, laterally outward direction 104, laterally anterior direction 106, and laterally posterior direction 108. As a more specific example, and as schematically illustrated in FIGS. 3-4, assembly interior side 212 of moisture capture assembly 200 may be described as being spaced apart from assembly exterior side 214 of the moisture capture assembly along transversely inward direction 110. As used herein, a first component may be described as being positioned on an interior side of a second component when the first component is at least partially offset from the second component along transversely inward direction 110. Similarly, as used herein, a first component may be described as being positioned on an exterior side of a second component when the first component is at least partially offset from the second component along transversely outward direction 112.

Although FIGS. 2-4 schematically illustrate garment 100 as being generally flat and/or planar, this is not required of garment 100 in all examples and/or configurations. Accordingly, it is within the scope of the present disclosure that each of laterally inward direction 102, laterally outward direction 104, laterally anterior direction 106, laterally posterior direction 108, transversely inward direction 110, and/or transversely outward direction 112 is not oriented in the same absolute direction at all locations on garment 100. Stated differently, laterally inward direction 102, laterally outward direction 104, laterally anterior direction 106, laterally posterior direction 108, transversely inward direction 110, and transversely outward direction 112 may be described as representing directions that are defined relative to a particular location and/or region of garment 100, irrespective of the configuration and/or orientation of the garment in a location and/or region away from such a particular location and/or region.

For purposes of clarity, the schematic cross-sectional illustrations of FIGS. 3-4 represent the illustrated components as having an extent that is exaggerated along the direction parallel to transversely inward direction 110 and transversely outward direction 112. Additionally, while FIGS. 3-4 illustrate the components of garment 100 as being slightly spaced apart from one another for clarity, it is to be understood various components of the assembled garment are drawn into direct contact with one another, such as via bonds 150. In the schematic illustrations of FIGS. 2-4, bonds 150 are schematically represented by jagged/zig-zag lines that are intended to represent the general regions in which the bonds are formed and the components through which optional stitches extend. However, such representations are not intended to imply or require that the bonds 150 are stitching seams or that optional stitching seams have a particular shape, form, or extent.

Although the cross-sectional views of FIGS. 3-4 are taken along the lines 3-3 and 4-4 of FIG. 2, it is to be understood that such cross-sectional views (including the cross-sectional views of FIGS. 11-13) may correspond to any suitable portion of garment 100 and/or of joined region 142. In this manner, the cross-sectional views of FIGS. 3-4 and/or 11-13 may be understood as being representative of any and/or every such location along a perimeter of moisture capture assembly 200. In particular, in some examples, the constructions illustrated in the cross-sectional views of FIGS. 3 and 11 extend fully (or at least substantially fully) across each garment lateral edge 124 in a region adjacent to moisture capture assembly 200. Similarly, in some examples, the constructions illustrated in the cross-sectional views of FIGS. 4 and 12 extend fully (or at least substantially fully) across the portions of joined region 142 corresponding to moisture capture assembly anterior edge 208 and/or moisture capture assembly posterior edge 210. However, this is not required of all examples of garment 100, and it additionally is within the scope of the present disclosure that the construction of garment 100 may vary at distinct locations along a perimeter of moisture capture assembly 200.

Garment 100 may include any of a variety of features for accommodating and/or engaging the wearer's body. In particular, in some examples, at least a portion of garment interior surface 120 is configured to directly contact the wearer when garment 100 is worn by the wearer. Stated differently, in some examples, garment 100 is configured such that, when the garment is worn by the wearer, no portion of the garment is positioned directly between garment interior surface 120 and the wearer. Similarly, in some examples, garment 100 is configured such that, when the garment is worn by the wearer, no portion of the garment is positioned distal the wearer relative to garment exterior surface 122.

Garment base 160 may feature any of a variety of constructions for supporting moisture capture assembly 200 within crotch region 140. In various examples, and as schematically illustrated in FIGS. 1-4 and less schematically illustrated in FIGS. 5-13, garment base 160 includes one or more base layers 162. In particular, in some examples, at least one base layer 162 is joined to at least a portion of moisture capture assembly 200 via a corresponding bond 150. Additionally or alternatively, and as schematically illustrated in FIGS. 1-2, garment base 160 may include a plurality of base panels 180 that are operatively coupled to one another to collectively form at least a portion of the garment base. In such examples, each base panel 180 may include and/or be at least one base layer 162. In such examples, the plurality of base panels 180 may be operatively coupled to one another in any of a variety of manners, such as via stitching and/or via adhesive bonding.

In various examples, and as schematically illustrated in FIGS. 1-4 and less schematically illustrated in FIGS. 5-13, base layer(s) 162 include an interior base layer 166 that forms at least a portion of garment interior surface 120 within crotch region 140 and/or an exterior base layer 168 that forms at least a portion of garment exterior surface 122 within the crotch region. Each base layer 162 (e.g., interior base layer 166 and/or exterior base layer 168) may be formed of any of a variety of materials. As examples, each base layer 162 may be at least partially formed of a natural fiber, cotton, a synthetic fiber, polyester, nylon, Spandex™ fabric, and/or combinations thereof.

In the present disclosure, each base layer 162 may be at least partially characterized with reference to one or more lateral edges thereof. For example, and as schematically illustrated in FIG. 3, each base layer 162 may be described as extending between and terminating at a pair of base layer lateral outward edges 164, such that the base layer extends away from each base layer lateral outward edge along laterally inward direction 102.

As used herein, directional terms such as "overlie," "above," "underlie," "below," and the like generally refer to relative positions as viewed from the side of garment 100 with garment interior surface 120 facing upwards, as in the schematic views of FIGS. 3-4. In particular, a first component may be described as overlying a second component, and/or as being positioned above the second component, when the first component is spatially offset from the second component along transversely inward direction 110. Similarly, a first component may be described as underlying a second component, and/or as being positioned under the second component, when the first component is spatially offset from the second component along transversely outward direction 112.

In some examples, and as schematically illustrated in FIG. 1 and less schematically illustrated in FIGS. 5-10, garment 100 includes a waistband region 126 (shown in FIGS. 1 and 5-6) and/or one or more garment apertures 130. In some examples, garment base 160 may at least partially define waistband region 126 and/or each garment aperture 130. In some examples, and as schematically illustrated in FIGS. 1-2 and less schematically illustrated in FIGS. 5-10, each garment aperture 130 defines a leg opening 132 that is configured to receive a leg of the wearer when garment 100 is worn by the wearer.

In some examples, and as schematically illustrated in FIGS. 1-3 and less schematically illustrated in FIGS. 5-11, garment 100 additionally includes an edge binding strip 134 positioned adjacent to each garment aperture 130. In some such examples, each edge binding strip 134 at least partially defines the respective garment aperture 130 and/or a respective leg opening 132 associated with the respective garment aperture 130. In some examples, and as schematically illustrated in FIG. 3 and less schematically illustrated in FIG. 11, each edge binding strip 134 extends around a respective moisture capture assembly lateral edge 206 from garment interior surface 120 to garment exterior surface 122. Stated differently, in some examples, each edge binding strip 134 wraps around and/or encloses at least a portion of the respective moisture capture assembly lateral edge 206.

In some examples, each edge binding strip 134 is formed of an elastic material and/or of the same material as at least a portion of garment base 160. Additionally or alternatively, in some examples, and as schematically illustrated in FIG. 3 and less schematically illustrated in FIG. 11, garment 100 includes a pair of elastic strips 136 such that each edge binding strip 134 at least substantially encloses, retains, and/or supports a respective elastic strip 136. In particular, each elastic strip 136 may include and/or be a material, such as an elastic rubber, that is configured to bias each edge binding strip 134 toward the wearer's leg to conform each leg opening 132 to the wearer's leg. In some examples, and as schematically illustrated in FIG. 3 and less schematically illustrated in FIG. 11, each elastic strip 136 underlies at least a portion of moisture capture assembly peripheral region 204 such that exterior base layer 168 is positioned between the elastic strip and moisture capture assembly 200. However, this is not required, and it additionally is within the scope of the present disclosure that each elastic strip 136 may overlie at least a portion of moisture capture assembly peripheral region 204 such that interior base layer 166 is positioned between the elastic strip and moisture capture assembly 200.

Moisture capture assembly 200 and/or moisture retention portion 220 may have any of a variety of constructions for absorbing and capturing moisture from the wearer. In some examples, and as schematically illustrated in FIGS. 3-4, moisture retention portion 220 includes one or more moisture retention layers 224, such as may include a first moisture retention layer 226 and a second moisture retention layer 228. In some such examples, and as schematically illustrated in FIG. 3, each moisture retention layer 224 extends to (and thus at least partially defines) a respective moisture retention portion lateral edge 222. When present, first moisture retention layer 226 and second moisture retention layer 228 may be formed of the same and/or similar materials, or may be at least partially formed of different materials. In some examples, first moisture retention layer 226 and second moisture retention layer 228 are operatively coupled to one another, such as via bond(s) 150.

In some examples, and as schematically illustrated in FIGS. 3-4, moisture capture assembly 200 and/or moisture retention portion 220 includes a wicking layer 230 that is configured to wick moisture away from the wearer. In particular, in such examples, wicking layer 230 may be configured to draw moisture away from the wearer, such as via capillary action, and to direct and/or convey the moisture to moisture retention layer(s) 224. In such examples, wicking layer 230 may be positioned and/or bonded within moisture capture assembly 200 in any of a variety of manners. For example, and as schematically illustrated in FIG. 3, wicking layer 230 may extend within each of moisture capture assembly central region 202 and moisture capture assembly peripheral region 204. In some examples, wicking layer 230 is operatively coupled to moisture retention portion 220, such as to first moisture retention layer 226. In some examples, and as schematically illustrated in FIG. 3, wicking layer 230 at least partially defines assembly interior side 212 of moisture capture assembly 200. In some examples, and as schematically illustrated in FIG. 3, interior base layer 166 overlies at least a portion of wicking layer 230 within moisture capture assembly central region 202 and/or within moisture capture assembly peripheral region 204.

Anti-leak portion 240 of moisture capture assembly 200 may include any of a variety of components and/or features for restricting moisture from exiting the moisture capture assembly. For example, and as schematically illustrated in FIGS. 3-4 and less schematically illustrated in FIGS. 11-13, anti-leak portion 240 may include and/or be a moisture barrier layer 242 that is operatively coupled to moisture retention portion 220. When present, moisture barrier layer 242 may include and/or be any of a variety of materials, such as a moisture-impermeable film and/or a polyurethane film. In some examples, moisture barrier layer 242 is operatively coupled to moisture retention portion 220 only in moisture capture assembly peripheral region 204 and/or in joined region 142.

In some examples, and as schematically illustrated in FIGS. 3-4 and less schematically illustrated in FIGS. 11-13, at least a portion of moisture barrier layer 242 underlies moisture retention portion 220. Specifically, in some such examples, the entirety of moisture barrier layer 242 underlies moisture retention portion 220. However, this is not required, and it additionally is within the scope of the present disclosure that a portion of moisture barrier layer 242 may overlie moisture retention portion 220, such as within moisture capture assembly peripheral region 204. Specifically, in some such examples, moisture barrier layer 242 underlies moisture retention portion 220 within moisture capture assembly central region 202 and extends around each moisture retention portion lateral edge 222 from assembly exterior side 214 to assembly interior side 212. In some examples, and as schematically illustrated in FIGS. 3-4 and less schematically illustrated in FIGS. 11-13, moisture barrier layer 242 at least partially defines assembly exterior side 214 of moisture capture assembly 200.

Additionally or alternatively, in some examples, and as schematically illustrated in FIGS. 3-4, anti-leak portion 240 may include and/or be a moisture barrier treatment 246 and/or a moisture barrier film that is applied to moisture retention portion 220, such as to moisture retention layer 224 (e.g., to second moisture retention layer 228, when present).

Each portion of moisture capture assembly 200 may be formed of any of a variety of materials. As examples, each of moisture capture assembly 200, moisture retention portion 220, first moisture retention layer 226, second moisture retention layer 228, wicking layer 230, and/or moisture barrier layer 242 may be at least partially formed of a natural fiber, cotton, a synthetic fiber, polyester, nylon, Spandex™ fabric, and/or combinations thereof.

With reference to the cross-sectional views of FIGS. 3-4 and 11, a configuration of moisture barrier layer 242 also may be characterized with reference to a moisture barrier layer lateral edge 244 thereof, which represents a terminal edge of the moisture barrier layer. For example, and as schematically illustrated in FIG. 3 and less schematically illustrated in FIG. 11, each moisture barrier layer lateral edge 244 may be aligned with a respective moisture retention portion lateral edge 222. However, this is not required of all examples of moisture capture assembly 200, and it additionally is within the scope of the present disclosure that each moisture barrier layer lateral edge 244 may be spaced apart from the respective moisture retention portion lateral edge 222 along laterally outward direction 104 or along laterally inward direction 102. In some examples, such as when moisture barrier layer lateral edge 244 is aligned with moisture retention portion lateral edge 222 or is spaced apart from the moisture retention portion lateral edge along laterally outward direction 104, the moisture barrier layer lateral edge may define moisture capture assembly lateral edge 206. Alternatively, in some examples, such as when moisture barrier layer lateral edge 244 is spaced apart from moisture retention portion lateral edge 222 along laterally inward direction 102, the moisture barrier layer lateral edge also may be spaced apart from moisture capture assembly lateral edge 206 along laterally inward direction 102.

As used herein, the term "aligned," as used to describe a relative position of a first edge relative to a second edge, generally refers to a configuration in which the first edge and the second edge are positioned at respective locations that are not spatially separated from one another along laterally inward direction 102 or along laterally outward direction 104, but which may be spatially separated from one another along transversely inward direction 110 or along transversely outward direction 112. However, it is to be understood that a description herein of two or more components as being "aligned" does not strictly require that the two or more components are exactly and/or precisely aligned with one another. For example, as known in the art, garment construction is not perfect, and the imprecision introduced by human- and/or machine-performed manufacturing can introduce slight misalignments between components that nominally are intended to be aligned with one another. Accordingly, for the purposes of the present disclosure, the term "aligned" is intended to encompass configurations in which the components are perfectly aligned, as well as configurations in which the components are slightly misaligned as a result of manufacturing tolerances.

When present, interior base layer 166 may have any suitable position, orientation, and/or extent relative to moisture capture assembly 200, moisture retention portion 220, anti-leak portion 240, and/or joined region 142. In some examples, and as schematically illustrated in FIGS. 3-4 and less schematically illustrated in FIGS. 11-13, at least a portion of interior base layer 166 overlies at least a portion of moisture capture assembly 200. For example, interior base layer 166 (or a portion thereof) may overlie at least a portion of moisture capture assembly peripheral region 204, at least a portion of moisture capture assembly central region 202, and/or a full width of moisture capture assembly 200. While FIGS. 3-4 schematically illustrate interior base layer 166 as overlying moisture capture assembly 200 as a single flat layer, this is not required of all examples of garment 100. As examples, it also is within the scope of the present disclosure that interior base layer 166 may be folded, doubled over, and/or otherwise characterized by two or more adjacent layers within a portion of moisture capture assembly peripheral region 204 within which interior base layer 166 overlies moisture capture assembly 200.

In some examples, and as schematically illustrated in FIGS. 3-4 and less schematically illustrated in FIG. 11, each base layer lateral outward edge 164 of interior base layer 166 is aligned with a respective moisture capture assembly lateral edge 206 and/or with a respective moisture retention portion lateral edge 222. In other examples, each base layer lateral outward edge 164 of interior base layer 166 may be spaced apart from the respective moisture capture assembly lateral edge 206 and/or from the respective moisture retention portion lateral edge 222 along laterally inward direction 102 or along laterally outward direction 104.

In some examples, a configuration of interior base layer 166 additionally or alternatively may be characterized with reference to moisture barrier layer 242. For example, and as schematically illustrated in FIGS. 3-4 and less schematically illustrated in FIGS. 11-13, interior base layer 166 may overlie at least a portion of moisture barrier layer 242 within moisture capture assembly peripheral region 204 and/or within moisture capture assembly central region 202. Additionally or alternatively, in some examples, and as schematically illustrated in FIGS. 3-4 and less schematically illustrated in FIG. 11, base layer lateral outward edge 164 of interior base layer 166 may be aligned with moisture barrier layer lateral edge 244. In other examples, base layer lateral outward edge 164 of interior base layer 166 may be spaced apart from moisture barrier layer lateral edge 244 along laterally inward direction 102 or along laterally outward direction 104.

When present, exterior base layer 168 may have any suitable position, orientation, and/or extent relative to moisture capture assembly 200, moisture retention portion 220, anti-leak portion 240, and/or joined region 142. In some examples, and as schematically illustrated in FIGS. 3-4 and less schematically illustrated in FIGS. 11-13, at least a portion of exterior base layer 168 underlies at least a portion of moisture capture assembly 200. For example, exterior base layer 168 (or a portion thereof) may underlie at least a portion of moisture capture assembly peripheral region 204, at least a portion of moisture capture assembly central region 202, and/or a full width of moisture capture assembly 200.

While FIGS. 3-4 schematically illustrate exterior base layer 168 as underlying moisture capture assembly 200 as a single flat layer, this is not required of all examples of garment 100. As examples, it also is within the scope of the present disclosure that exterior base layer 168 may be folded, doubled over, and/or otherwise characterized by two or more adjacent layers within a portion of moisture capture assembly peripheral region 204 within which exterior base layer 168 underlies moisture capture assembly 200.

In some examples, and as schematically illustrated in FIGS. 3-4 and less schematically illustrated in FIG. 11, each base layer lateral outward edge 164 of exterior base layer 168 is aligned with a respective moisture capture assembly lateral edge 206 and/or with a respective moisture retention portion lateral edge 222. In other examples, base layer lateral outward edge 164 of exterior base layer 168 may be spaced apart from the respective moisture capture assembly lateral edge 206 and/or from the respective moisture retention portion lateral edge 222 along laterally inward direction 102 or along laterally outward direction 104.

In some examples, a configuration of exterior base layer 168 additionally or alternatively may be characterized with reference to moisture barrier layer 242. For example, and as schematically illustrated in FIGS. 3-4 and less schematically illustrated in FIGS. 11-13, exterior base layer 168 may underlie at least a portion of moisture barrier layer 242 within moisture capture assembly peripheral region 204 and/or within moisture capture assembly central region 202. Additionally or alternatively, in some examples, and as schematically illustrated in FIGS. 3-4 and less schematically illustrated in FIG. 11, base layer lateral outward edge 164 of exterior base layer 168 may be aligned with moisture barrier layer lateral edge 244. In other examples, base layer lateral outward edge 164 of exterior base layer 168 may be spaced apart from moisture barrier layer lateral edge 244 along laterally inward direction 102 or along laterally outward direction 104.

In examples in which the plurality of base layers 162 includes interior base layer 166 and exterior base layer 168, the interior base layer and the exterior base layer may have any suitable relative orientation. As examples, each base layer lateral outward edge 164 of interior base layer 166 may be aligned with a respective base layer lateral outward edge 164 of exterior base layer 168, or may be spaced apart from the respective base layer lateral outward edge of the exterior base layer. More specifically, the base layer lateral outward edge of the interior base layer may be spaced apart from the base layer lateral outward edge of the exterior base layer along laterally inward direction 102 or along laterally outward direction 104. In particular, FIGS. 3 and 11 illustrate examples in which base layer lateral outward edge 164 of interior base layer 166 is approximately aligned with base layer lateral outward edge 164 of exterior base layer 168.

As discussed, moisture capture assembly 200 is joined to garment base 160 via one or more bonds 150 formed within joined region 142. Specifically, in some examples, and as schematically illustrated in FIGS. 2-3 and less schematically illustrated in FIG. 11, bonds 150 include a pair of lateral region bonds 152, each of which joins a respective moisture capture assembly lateral edge 206 to garment base 160. Additionally or alternatively, in some examples, and as schematically illustrated in FIGS. 2 and 4 and less schematically illustrated in FIG. 12, bonds 150 include an anterior region bond 154 that joins moisture capture assembly anterior edge 208 to garment base 160. Additionally or alternatively, in some examples, and as schematically illustrated in FIGS. 2 and 4 and less schematically illustrated in FIG. 13, bonds 150 include a posterior region bond 156 that joins moisture capture assembly posterior edge 210 to garment base 160.

Each lateral region bond may have any suitable form for joining components of garment 100 as described herein. In some examples, and as schematically illustrated in FIG. 3, each lateral region bond 152 joins moisture capture assembly 200 to each of interior base layer 166 and exterior base layer 168. However, this is not required of all examples of garment 100, and it additionally is within the scope of the present disclosure that each lateral region bond 152 may join moisture capture assembly 200 to only one of interior base layer 166 or exterior base layer 168. In some examples, and as schematically illustrated in FIG. 3, interior base layer 166 and/or exterior base layer 168 extend within crotch region 140 and terminate at, or proximal to, each lateral region bond 152. In this manner, in such examples, the pair of lateral region bonds 152 may be described as representing, or as being located proximal to, the terminal lateral edges of garment base 160 within crotch region 140.

In an example in which garment 100 includes the pair of edge binding strips 134, and as schematically illustrated in FIGS. 2-3 and less schematically illustrated in FIG. 11, bonds 150 further may include a pair of edge binding strip bonds 158. In particular, in such examples, each edge binding strip bond 158 may include stitching that passes through each of interior base layer 166, moisture capture assembly 200, exterior base layer 168, and a respective edge binding strip 134 to join the respective edge binding strip to the garment base. In some such examples, and as schematically illustrated in FIG. 3 and less schematically illustrated in FIG. 11, each edge binding strip bond 158 is aligned with, and/or at least partially overlaps, a respective lateral region bond 152. In other examples, each edge binding strip bond 158 may be laterally offset relative to the respective lateral region bond 152, such as along laterally inward direction 102 or laterally outward direction 104. In examples in which garment 100 further includes elastic strip 136, and as schematically illustrated in FIG. 3 and less schematically illustrated in FIG. 11, each edge binding strip bond 158 may include stitching that passes through a respective elastic strip 136 to join the respective elastic strip to garment base 160.

Anterior region bond 154 may have any suitable form for joining components of garment 100 as described herein. In some examples, and as schematically illustrated in FIG. 4 and less schematically illustrated in FIG. 12, anterior region bond 154 joins moisture capture assembly 200 to only one of interior base layer 166 or exterior base layer 168. In particular, in the example of FIGS. 4 and 12, anterior region bond 154 joins moisture capture assembly 200 to interior base layer 166 but does not join the moisture capture assembly to exterior base layer 168, such that the exterior base layer is uncoupled from the moisture capture assembly proximal to the anterior region bond. However, this is not required, and it additionally is within the scope of the present disclosure that anterior region bond 154 may join moisture capture assembly 200 to each of interior base layer 166 and exterior base layer 168.

In some examples, anterior region bond 154 may be described as representing an anterior edge and/or boundary of crotch region 140. In some such examples, and as schematically illustrated in FIG. 4 and less schematically illustrated in FIG. 12, interior base layer 166 and/or exterior base layer 168 extends within crotch region 140 and further extends away from the crotch region along laterally anterior direction 106. Stated differently, in such examples, interior base layer 166 and/or exterior base layer 168 does not terminate at (or proximal to) anterior region bond 154, but instead extends continuously across the anterior region bond (and/or across a region of garment 100 proximal to the anterior region bond). However, this is not required of all examples of garment 100, and it additionally is within the scope of the present disclosure that interior base layer 166 and/or exterior base layer 168 may extend within crotch region 140 and terminate at, or proximal to, anterior region bond 154.

Posterior region bond 156 may have any suitable form for joining components of garment 100 as described herein. In some examples, and as schematically illustrated in FIG. 4 and less schematically illustrated in FIG. 13, posterior region bond 156 joins moisture capture assembly 200 to each of interior base layer 166 and exterior base layer 168. However, this is not required of all examples of garment 100, and it additionally is within the scope of the present disclosure that posterior region bond 156 may join moisture capture assembly 200 to only one of interior base layer 166 or exterior base layer 168.

In some examples, posterior region bond 156 may be described as representing a posterior edge and/or boundary of crotch region 140. In some examples, and as schematically illustrated in FIG. 4 and less schematically illustrated in FIG. 13, interior base layer 166 and/or exterior base layer 168 extends within crotch region 140 and terminates at, or proximal to, posterior region bond 156. However, this is not required of all examples of garment 100, and it additionally is within the scope of the present disclosure that interior base layer 166 and/or exterior base layer 168 may extend within crotch region 140 and further may extend away from the crotch region along laterally posterior direction 108. Stated differently, in such examples, interior base layer 166 and/or exterior base layer 168 do not terminate at (or proximal to) posterior region bond 156, but instead extend continuously across the posterior region bond (and/or across a region of garment 100 proximal to the posterior region bond).

In some examples, such as in an example in which interior base layer 166 and/or exterior base layer 168 terminates at, or proximal to, posterior region bond 156, base layers 162 additionally include one or more connected base layers 170. In particular, in such examples, and as schematically illustrated in FIG. 4 and less schematically illustrated in FIG. 13, each connected base layer 170 is joined to moisture capture assembly 200 by anterior region bond 154 and/or by posterior region bond 156 and does not extend within crotch region 140. More specifically, in the examples of FIGS. 4 and 13, each connected base layer 170 is joined to moisture capture assembly 200 and to each of interior base layer 166 and exterior base layer 168 by posterior region bond 156.

In some examples, and as schematically illustrated in FIG. 4 and less schematically illustrated in FIG. 13, connected base layer(s) 170 include an interior connected base layer 172 that extends immediately adjacent to interior base layer 166 at anterior region bond 154 and/or at posterior region bond 156. More specifically, in some such examples, interior connected base layer 172 directly engages interior base layer 166. Similarly, in some examples, and as schematically illustrated in FIG. 4 and less schematically illustrated in FIG. 13, connected base layer(s) 170 include an exterior connected base layer 174 that extends immediately adjacent to exterior base layer 168 at anterior region bond 154 and/or at posterior region bond 156. More specifically, in some such examples, exterior connected base layer 174 directly engages exterior base layer 168. In some examples, each connected base layer 170 (e.g., each of interior connected base layer 172 and exterior connected base layer 174) operates to at least partially conceal anterior region bond 154 and/or posterior region bond 156. Specifically, in the example of FIGS. 4 and 13, each of interior connected base layer 172 and exterior connected base layer 174 is folded over an otherwise exposed portion of posterior region bond 156, thereby concealing the posterior region bond from view.

Additionally or alternatively, in some examples, and as schematically illustrated in FIG. 4, posterior region bond 156 may be described as joining moisture capture assembly 200, interior base layer 166, and exterior base layer 168 to a pair of base panels 180. In such examples, the pair of base panels 180 joined by posterior region bond 156 may extend away from crotch region 140, and/or may operate to at least partially conceal the posterior region bond. In some examples, the pair of base panels 180 joined by posterior region bond 156 may include and/or be interior connected base layer 172 and/or exterior connected base layer 174.

Turning more specifically to first example garment 1000 illustrated in FIGS. 5-7 and 11-13, first example garment 1000 represents an example of garment 100 in the form of an article of swimwear, and specifically a swimwear bottom. In particular, FIGS. 5-7 illustrate various aspects of the outer surfaces of first example garment 1000. FIGS. 11-13 are cross-sectional views illustrating the configurations of base layers 162 of first example garment 1000 and of the components of moisture capture assembly 200 within joined region 142 and/or within moisture capture assembly peripheral region 204 of first example garment 1000. As discussed, it is to be understood that the configurations illustrated in FIGS. 11-13 may be exhibited at any of a variety of locations along moisture capture assembly peripheral region 204. For example, the configuration illustrated in FIG. 11 may be representative of every location along moisture capture assembly lateral edge 206, or may be representative of only a portion of the moisture capture assembly lateral edge. Similarly, the configurations illustrated in FIGS. 12-13 may be representative of every location along moisture capture assembly anterior edge 208 and moisture capture assembly posterior edge 210, respectively, or may be representative of only a portion of the moisture capture assembly anterior edge or the moisture capture assembly posterior edge.

As illustrated in FIGS. 5-7 and 11, first example garment 1000 includes edge binding strip 134 positioned adjacent to each garment aperture 130, such that each edge binding strip at least partially defines the corresponding garment aperture and the corresponding leg opening 132. Turning more specifically to the cross-sectional views of FIGS. 11-13, moisture retention portion 220 of first example garment 1000 includes a single moisture retention layer, and anti-leak portion 240 includes moisture barrier layer 242 in the form of a moisture-impermeable film that is joined to moisture retention portion 220 by bonds 150. As illustrated in FIGS. 5-7 and 11-13, garment base 160 of first example garment 1000 includes interior base layer 166, exterior base layer 168, and a pair of connected base layers 170 (shown in FIG. 13).

Turning to second example garment 2000 illustrated in FIGS. 8-13, second example garment 2000 represents an example of garment 100 in the form of an another article of swimwear, and specifically a one-piece swimsuit. In particular, FIGS. 8-10 illustrate various aspects of the outer surfaces of second example garment 2000. As shown in FIGS. 8-10, second example garment 2000 includes torso region 50 that includes a pair of breast cups 52 and a pair of shoulder straps 54.

As with first example garment 1000, FIGS. 11-13 are cross-sectional views illustrating the configurations of base layers 162 of second example garment 2000 and of the components of moisture capture assembly 200 within joined region 142 and/or within moisture capture assembly peripheral region 204 of second example garment 2000. Stated differently, each of first example garment 1000 and second example garment 2000 features the constructions illustrated in FIGS. 11-13. Accordingly it is to be understood that the foregoing description of FIGS. 11-13 with reference to first example garment 1000 also applies to the configuration of second example garment 2000.

Figure 14:
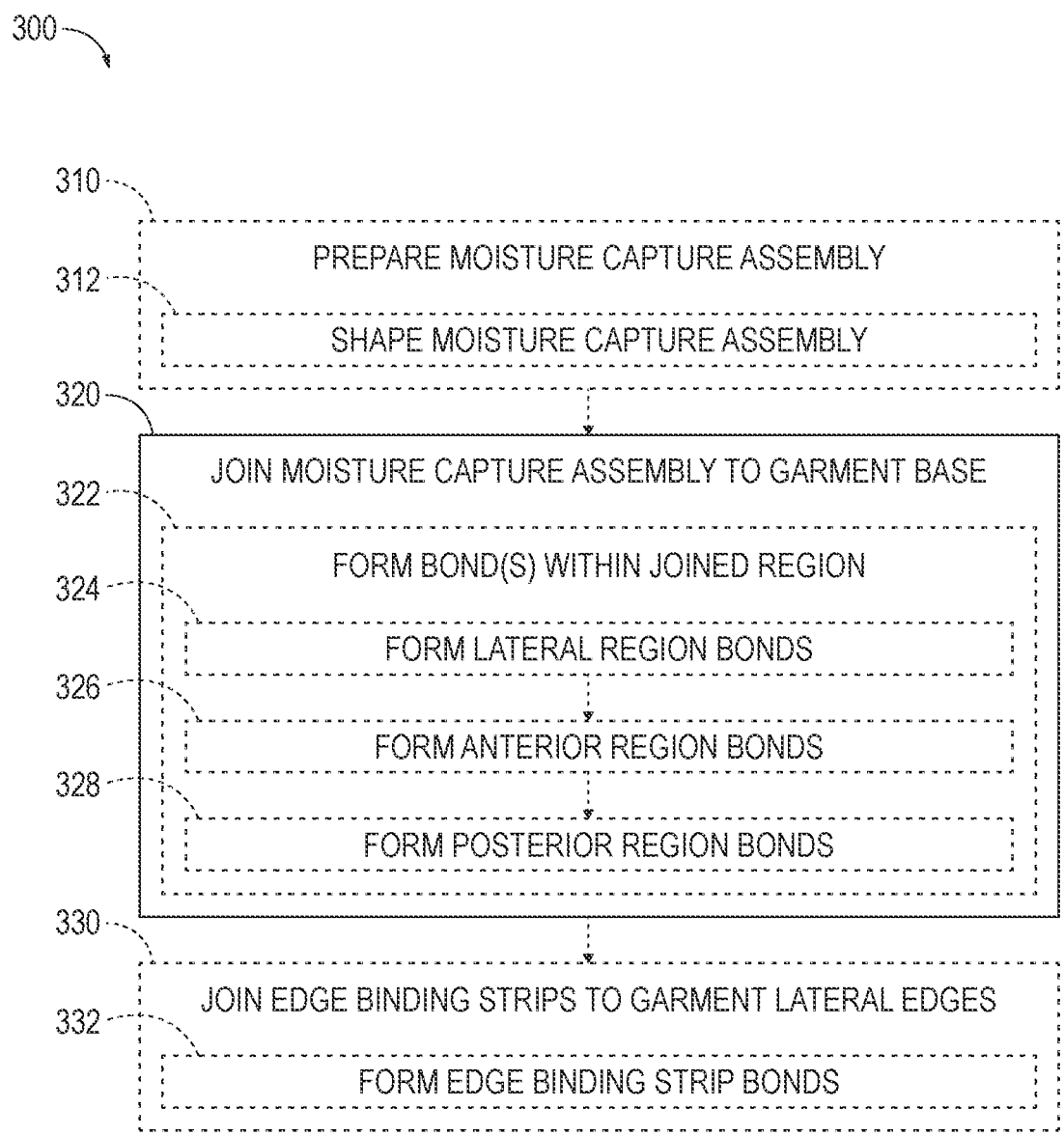
FIG. 14 is a flowchart depicting methods of manufacturing a garment according to the present disclosure.

FIG. 14 is a flowchart depicting a method 300, according to the present disclosure, of manufacturing a garment, such as garment 100, first example garment 1000, and/or second example garment 2000 disclosed herein. As shown in FIG. 14, method 300 includes joining, at 320, a moisture capture assembly to a garment base within at least a joined region of the garment. Examples of moisture capture assemblies, of garment bases, and/or of joined regions that may be utilized in conjunction with methods 300 are disclosed herein with reference to moisture capture assembly 200, garment base 160, and/or joined region 142, respectively. In particular, in examples of method 300 according to the present disclosure, the moisture capture assembly generally includes a moisture retention portion configured to absorb and retain moisture from the wearer and an anti-leak portion configured to restrict moisture from exiting the moisture retention portion. Examples of moisture retention portions and/or of anti-leak portions that may be utilized in conjunction with methods 300 are disclosed herein with reference to moisture retention portion 220 and/or anti-leak portion 240, respectively.

The joining the moisture capture assembly to the garment base at 320 may be performed in any suitable manner according to the present disclosure. In particular, in some examples, and as shown in FIG. 14, the joining the moisture capture assembly to the garment base at 320 includes forming, at 322, one or more bonds (such as any suitable bonds 150 disclosed herein) within the joined region. More specifically, in some examples, and as shown in FIG. 14, the forming the one or more bonds at 322 includes forming, at 324, a pair of lateral region bonds, forming, at 326, an anterior region bond, and/or forming, at 328, a posterior region bond. Examples of lateral region bonds, of anterior region bonds, and/or of posterior region bonds that may be utilized in conjunction with methods 300 are disclosed herein with reference to lateral region bond 152, anterior region bond 154, and/or posterior region bond 156, respectively.

In some examples, the moisture capture assembly includes a moisture capture assembly peripheral region (such as moisture capture assembly peripheral region 204 disclosed herein), which in turn includes a pair of moisture capture assembly lateral edges (such as moisture capture assembly lateral edges 206 disclosed herein). In some such examples, the forming the pair of lateral region bonds at 324 includes forming each lateral region bond at a respective moisture capture assembly lateral edge. Similarly, in some examples, the moisture capture assembly peripheral region includes a moisture capture assembly anterior edge (such as moisture capture assembly anterior edge 208 disclosed herein) and/or a moisture capture assembly posterior edge (such as moisture capture assembly posterior edge 210 disclosed herein). In some such examples, the forming the anterior region bond at 326 includes forming the anterior region bond at the moisture capture assembly anterior edge, and/or the forming the posterior region bond at 328 includes forming the posterior region bond at the moisture capture assembly posterior edge.

In some examples, the joining the moisture capture assembly to the garment base at 320 includes joining two or more layers of the moisture capture assembly to one another. More specifically, in some examples, the joining the moisture capture assembly to the garment base at 320 includes joining two or more of a moisture retention portion, an anti-leak portion, one or more moisture retention layers, a first moisture retention layer, a second moisture retention layer, a wicking layer, and/or a moisture barrier layer to one another. In such examples, joining two or more layers of the moisture capture assembly to one another may include, or may be a result of, one or more other steps of the joining the moisture capture assembly to the garment base at 320, such as the forming the bonds within the joined region at 322. Stated differently, in some examples, a step that operates to join the moisture capture assembly to the garment base also may operate to join two or more layers of the moisture capture assembly to one another. Accordingly, in some examples, the joining the moisture capture assembly to the garment base at 320 includes, prior to the forming the bond(s) at 322, positioning the layers of the moisture capture assembly between the interior base layer and the exterior base layer. Examples of moisture retention portions, anti-leak portions, moisture retention layers, first moisture retention layers, second moisture retention layers, wicking layers, moisture barrier layers, interior base layers, and/or exterior base layers that may be utilized in conjunction with methods 300 are disclosed herein with reference to moisture retention portion 220, anti-leak portion 240, moisture retention layer(s) 224, first moisture retention layer 226, second moisture retention layer 228, wicking layer 230, moisture barrier layer 242, interior base layer 166, and/or exterior base layer 168, respectively.

In some examples, the garment includes a pair of edge binding strips (such as edge binding strips 134 disclosed herein) positioned adjacent to garment lateral edges of the garment (such as garment lateral edges 124 disclosed herein). In some such examples, and as shown in FIG. 14, method 300 further includes joining, at 330, each edge binding strip to a respective garment lateral edge. The joining each edge binding strip to the respective garment lateral edge at 330 may be performed in any suitable manner. For example, the joining each edge binding strip to the respective garment lateral edge at 330 may be performed subsequent to the joining the moisture capture assembly to the garment base at 320. Additionally or alternatively, in some examples, and as shown in FIG. 14, the joining each edge binding strip to the respective garment lateral edge at 330 includes forming, at 332, a pair of edge binding strip bonds, such as edge binding strip bonds 158 disclosed herein. Additionally or alternatively, in some examples, the joining each edge binding strip to the respective garment lateral edge at 330 includes joining a pair of elastic strips (such as elastic strips 136 disclosed herein) to the pair of garment lateral edges, such as with the pair of edge binding strip bonds. That is, in some such examples, the forming the pair of edge binding strip bonds at 332 includes joining the pair of elastic strips to the pair of garment lateral edges.

In some examples, the joining the moisture capture assembly to the garment base at 320 includes joining a moisture capture assembly that is at least partially preformed to the garment base. More specifically, in some examples, and as shown in FIG. 14, method 300 further includes, prior to the joining the moisture capture assembly to the garment base at 320, preparing, at 310, the moisture capture assembly.

The preparing the moisture capture assembly at 310 may be performed in any suitable manner. In some examples, and as shown in FIG. 14, the preparing the moisture capture assembly at 310 includes shaping, at 312, the moisture capture assembly, such as to adapt the moisture capture assembly for incorporation with the garment base. The shaping the moisture capture assembly at 312 may be performed in any of a variety of manners. As an example, the shaping the moisture capture assembly at 312 may include cutting the moisture capture assembly to a desired shape, such as a shape corresponding to a crotch region of the garment. More specifically, in some such examples, the shaping the moisture capture assembly at 312 includes utilizing a die cutting process.

Illustrative, non-exclusive examples of inventive subject matter according to the present disclosure are described in the following enumerated paragraphs:

A1. A garment configured to be worn by a wearer, the garment comprising:
 a joined region;
 a garment base; and
 a moisture capture assembly joined to the garment base within at least the joined region;
 wherein the moisture capture assembly includes:
  an assembly interior side that faces the wearer when the garment is worn by the wearer;
  an assembly exterior side that faces away from the wearer when the garment is worn by the wearer;
  a moisture retention portion configured to absorb and retain moisture from the wearer; and
  an anti-leak portion configured to restrict moisture from exiting the moisture retention portion; and
 wherein the moisture capture assembly is joined to the garment base via one or more bonds, optionally stitching seams, formed within the joined region.

A2. The garment of paragraph A1, further comprising a crotch region; wherein the moisture capture assembly is positioned at least partially within the crotch region.

A3. The garment of any of paragraphs A1-A2, wherein the garment base supports the moisture capture assembly, optionally within a/the crotch region.

A4. The garment of any of paragraphs A1-A3 further comprising:
 a garment interior surface that faces the wearer when the garment is worn by the wearer; and
 a garment exterior surface that faces away from the wearer when the garment is worn by the wearer.

A4.1. The garment of paragraph A4, wherein at least a portion of the garment interior surface is configured to directly contact the wearer when the garment is worn by the wearer.

A4.2. The garment of any of paragraphs A4-A4.1, wherein the garment is configured such that, when the garment is worn by the wearer, no portion of the garment is positioned directly between the garment interior surface and the wearer.

A4.3. The garment of any of paragraphs A4-A4.2, wherein the garment is configured such that, when the garment is worn by the wearer, no portion of the garment is positioned distal the wearer relative to the garment exterior surface.

A5. The garment of any of paragraphs A1-A4.3, further comprising a waistband region; and optionally wherein the garment base at least partially defines the waistband region.

A6. The garment of any of paragraphs A1-A5, wherein the garment defines one or more garment apertures; and optionally wherein the garment base at least partially defines the one or more garment apertures.

A6.1. The garment of paragraph A6, wherein at least one garment aperture of the one or more garment apertures defines a leg opening that is configured to receive a leg of the wearer when the garment is worn by the wearer.

A7. The garment of any of paragraphs A1-A6.1, wherein the moisture capture assembly includes a moisture capture assembly central region and a moisture capture assembly peripheral region that circumferentially encloses the moisture capture assembly central region; and wherein the joined region includes at least a portion of the moisture capture assembly peripheral region.

A8. The garment of any of paragraphs A1-A7, wherein the moisture capture assembly extends between and terminates at a pair of moisture capture assembly lateral edges; and optionally wherein a/the moisture capture assembly peripheral region includes each moisture capture assembly lateral edge.

A8.1. The garment of paragraph A8, wherein the one or more bonds includes a pair of lateral region bonds; and wherein each lateral region bond of the pair of lateral region bonds joins a respective moisture capture assembly lateral edge of the pair of moisture capture assembly lateral edges to the garment base.

A9. The garment of any of paragraphs A1-A8.1, wherein the moisture capture assembly extends between and terminates at each of a moisture capture assembly anterior edge and a moisture capture assembly posterior edge.

A9.1. The garment of paragraph A9, wherein the one or more bonds includes:

an anterior region bond that joins the moisture capture assembly anterior edge to the garment base; and a posterior region bond that joins the moisture capture assembly posterior edge to the garment base.

A10. The garment of any of paragraphs A1-A9.1, wherein the joined region extends at least substantially around a perimeter of a/the moisture capture assembly peripheral region.

A11. The garment of any of paragraphs A1-A10, wherein the garment includes a pair of garment lateral edges in a region proximal to the moisture capture assembly; and wherein at least a portion of the moisture capture assembly extends away from each garment lateral edge along a laterally inward direction that is directed from the garment lateral edge toward a/the moisture capture assembly central region.

A12. The garment of any of paragraphs A1-A11, wherein the moisture retention portion extends between and terminates at a pair of moisture retention portion lateral edges; and wherein one of:

(i) each moisture capture assembly lateral edge of a/the pair of moisture capture assembly lateral edges is spaced apart from a respective moisture retention portion lateral edge of the pair of moisture retention portion lateral edges along a laterally outward direction that is directed from a/the moisture capture assembly central region toward a respective garment lateral edge of a/the pair of garment lateral edges; or (ii) each moisture retention portion lateral edge of the pair of moisture retention portion lateral edges defines a respective moisture capture assembly lateral edge of the pair of moisture capture assembly lateral edges.

A13. The garment of any of paragraphs A1-A12, wherein the garment base includes one or more base layers.

A13.1. The garment of paragraph A13, wherein each base layer of the one or more base layers extends between and terminates at a pair of base layer lateral outward edges, such that the base layer extends away from each base layer lateral outward edge along a/the laterally inward direction.

A13.2. The garment of any of paragraphs A13-A13.1, wherein the one or more base layers includes an interior base layer that forms at least a portion of a/the garment interior surface within a/the crotch region.

A13.2.1. The garment of paragraph A13.2, wherein at least a portion of the interior base layer overlies at least a portion of the moisture capture assembly; optionally wherein at least a portion of the interior base layer overlies at least a portion of a/the moisture capture assembly peripheral region; and optionally wherein at least a portion of the interior base layer overlies at least a portion of a/the moisture capture assembly central region.

A13.2.2. The garment of paragraph A13.2.1, wherein the interior base layer overlies a full width of the moisture capture assembly.

A13.2.3. The garment of any of paragraphs A13.2-A13.2.2, wherein each base layer lateral outward edge of a/the pair of base layer lateral outward edges of the interior base layer is one of:

(i) aligned with one or both of a respective moisture capture assembly lateral edge of a/the pair of moisture capture assembly lateral edges and a respective moisture retention portion lateral edge of a/the pair of moisture retention portion lateral edges;

(ii) spaced apart from one or both of the respective moisture capture assembly lateral edge and the respective moisture retention portion lateral edge along a/the laterally outward direction; or spaced apart from one or both of the respective moisture capture assembly lateral edge and the respective moisture retention portion lateral edge along a/the laterally inward direction.

A13.3. The garment of any of paragraphs A13-A13.2.3, wherein the one or more base layers includes an exterior base layer that forms at least a portion of a/the garment exterior surface within a/the crotch region.

A13.3.1. The garment of paragraph A13.3, wherein at least a portion of the exterior base layer underlies at least a portion of the moisture capture assembly; optionally wherein at least a portion of the exterior base layer underlies at least a portion of a/the moisture capture assembly peripheral region; and optionally wherein at least a portion of the exterior base layer underlies at least a portion of a/the moisture capture assembly central region.

A13.3.2. The garment of paragraph A13.3.1, wherein the exterior base layer underlies a/the full width of the moisture capture assembly.

A14. The garment of any of paragraphs A1-A13.3.2, wherein the garment base includes a plurality of base panels that are operatively coupled to one another.

A14.1. The garment of paragraph A14, wherein each base panel of the plurality of base panels includes at least one base layer of a/the one or more base layers.

A14.2. The garment of any of paragraphs A14-A14.1, wherein two or more base panels of the plurality of base panels are operatively coupled to one another at least partially via stitching.

A15. The garment of any of paragraphs A1-A14.2, wherein each base layer lateral outward edge of a/the pair of base layer lateral outward edges of an/the exterior base layer is one of:

(i) aligned with one or both of a respective moisture capture assembly lateral edge of a/the pair of moisture capture assembly lateral edges and a respective moisture retention portion lateral edge of a/the pair of moisture retention portion lateral edges;

(ii) spaced apart from one or both of the respective moisture capture assembly lateral edge and the respective moisture retention portion lateral edge along a/the laterally outward direction; or (iii) spaced apart from one or both of the respective moisture capture assembly lateral edge and the respective moisture retention portion lateral edge along a/the laterally inward direction.

A16. The garment of any of paragraphs A1-A15, wherein each base layer lateral outward edge of a/the pair of base layer lateral outward edges of an/the interior base layer is aligned with a respective base layer lateral outward edge of the pair of base layer lateral outward edges of an/the exterior base layer.

A17. The garment of any of paragraphs A1-A15, wherein each base layer lateral outward edge of a/the pair of base layer lateral outward edges of an/the interior base layer is spaced apart from a respective base layer lateral outward edge of the pair of base layer lateral outward edges of the exterior base layer along a/the laterally inward direction.

A18. The garment of any of paragraphs A1-A15, wherein each base layer lateral outward edge of a/the pair of base layer lateral outward edges of an/the interior base layer is spaced apart from a respective base layer lateral outward edge of the pair of base layer lateral outward edges of the exterior base layer along a/the laterally outward direction.

A19. The garment of any of paragraphs A1-A18, further comprising a pair of edge binding strips; wherein each edge binding strip is positioned adjacent to a respective garment aperture of a/the one or more garment apertures.

A19.1. The garment of paragraph A19, wherein each edge binding strip of the pair of edge binding strips at least partially defines the respective garment aperture; and optionally wherein the edge binding strip at least partially defines a/the leg opening.

A19.2. The garment of any of paragraphs A19-A19.1, wherein each edge binding strip of the pair of edge binding strips extends around a respective moisture capture assembly portion lateral edge of a/the pair of moisture capture assembly lateral edges from a/the garment interior surface to a/the garment exterior surface.

A19.3. The garment of any of paragraphs A19-A19.2, wherein each edge binding strip of the pair of edge binding strips encloses at least a portion of a/the respective moisture capture assembly lateral edge of a/the pair of moisture capture assembly lateral edges.

A19.4. The garment of any of paragraphs A19-A19.3, wherein each edge binding strip of the pair of edge binding strips is formed of an elastic material.

A19.5. The garment of any of paragraphs A19-A19.4, wherein each edge binding strip of the pair of edge binding strips is formed of the same material as at least a portion of the garment base.

A19.6. The garment of any of paragraphs A19-A19.5, further comprising a pair of elastic strips; wherein each edge binding strip of the pair of edge binding strips at least substantially encloses a respective elastic strip of the pair of elastic strips.

A19.6.1. The garment of paragraph A19.6, wherein each elastic strip of the pair of elastic strips underlies at least a portion of a/the moisture capture assembly peripheral region such that a/the exterior base layer is positioned between the elastic strip and the moisture capture assembly.

A19.6.2. The garment of any of paragraphs A19.6-A19.6.1, wherein each elastic strip of the pair of elastic strips overlies at least a portion of a/the moisture capture assembly peripheral region such that a/the interior base layer is positioned between the elastic strip and the moisture capture assembly.

A20. The garment of any of paragraphs A1-A19.6.2, wherein the moisture retention portion includes one or more moisture retention layers.

A20.1. The garment of paragraph A20, wherein each moisture retention layer of the one or more moisture retention layers extends to a respective moisture retention portion lateral edge of a/the pair of moisture retention portion lateral edges.

A20.2. The garment of any of paragraphs A20-A20.1, wherein the one or more moisture retention layers includes a first moisture retention layer and a second moisture retention layer.

A20.2.1. The garment of paragraph A20.2, wherein the first moisture retention layer and the second moisture retention layer are operatively coupled to one another.

A20.2.2. The garment of any of paragraphs A20.2-A20.2.1, wherein the first moisture retention layer and the second moisture retention layer are at least partially formed of different materials.

A21. The garment of any of paragraphs A1-A20.2.2, wherein the moisture capture assembly includes a wicking layer configured to wick moisture away from the wearer.

A21.1. The garment of paragraph A21, wherein the wicking layer extends within each of a/the moisture capture assembly central region and a/the moisture capture assembly peripheral region.

A21.2. The garment of any of paragraphs A21-A21.1, wherein the wicking layer is operatively coupled to the moisture retention portion, and optionally to a/the first moisture retention layer.

A21.3. The garment of any of paragraphs A21-A21.2, wherein an/the interior base layer overlies at least a portion of the wicking layer within one or both of a/the moisture capture assembly central region and a/the moisture capture assembly peripheral region.

A22. The garment of any of paragraphs A1-A21.3, wherein the anti-leak portion includes, and optionally is, a moisture barrier layer that is operatively coupled to the moisture retention portion.

A22.1. The garment of paragraph A22, wherein the moisture barrier layer is operatively coupled to the moisture retention portion only in one or both of a/the moisture capture assembly peripheral region and a/the joined region.

A22.2. The garment of any of paragraphs A22-A22.1, wherein at least a portion of the moisture barrier layer underlies the moisture retention portion.

A22.3. The garment of any of paragraphs A22-A22.2, wherein a portion of the moisture barrier layer overlies the moisture retention portion, optionally within a/the moisture capture assembly peripheral region.

A22.3.1. The garment of paragraph A22.3, wherein the moisture barrier layer extends around each moisture retention portion lateral edge of a/the pair of moisture retention portion lateral edges from the assembly exterior side to the assembly interior side.

A22.4. The garment of any of paragraphs A22-A22.3.1, wherein the moisture barrier layer includes, and optionally is, a film, optionally a polyurethane film.

A22.5. The garment of any of paragraphs A22-A22.4, wherein the moisture barrier layer extends between and terminates at a pair of moisture barrier layer lateral edges.

A22.5.1. The garment of paragraph A22.5, wherein each moisture barrier layer lateral edge is one of:

(i) aligned with a respective moisture retention portion lateral edge of a/the pair of moisture retention portion lateral edges;

(ii) spaced apart from the respective moisture retention portion lateral edge along a/the laterally inward direction; or (iii) spaced apart from the respective moisture retention portion lateral edge along a/the laterally outward direction.

A22.5.2. The garment of any of paragraphs A22.5-A22.5.1, wherein each moisture barrier layer lateral edge at least partially defines a respective moisture capture assembly lateral edge of a/the pair of moisture capture assembly lateral edges.

A22.5.3. The garment of any of paragraphs A22.5-A22.5.1, wherein each moisture barrier layer lateral edge is spaced apart from a respective moisture capture assembly lateral edge of a/the pair of moisture capture assembly lateral edges along a/the laterally inward direction.

A23. The garment of any of paragraphs A1-A22.5.3, wherein the anti-leak portion includes, and optionally is, one or both of a moisture barrier treatment and a moisture barrier film that is applied to the moisture retention portion.

A24. The garment of any of paragraphs A1-A23, wherein a/the one or more base layers includes an/the interior base layer; wherein the anti-leak portion includes a/the moisture barrier layer; and wherein the interior base layer overlies at least a portion of the moisture barrier layer within one or both of a/the moisture capture assembly peripheral region and a/the moisture capture assembly central region.

A25. The garment of any of paragraphs A1-A24, wherein a/the one or more base layers includes an/the interior base layer; wherein the anti-leak portion includes a/the moisture barrier layer; and wherein a/the base layer lateral outward edge of the interior base layer is aligned with a/the moisture barrier layer lateral edge.

A26. The garment of any of paragraphs A1-A24, wherein a/the one or more base layers includes an/the interior base layer; wherein the anti-leak portion includes a/the moisture barrier layer; and wherein a/the base layer lateral outward edge of the interior base layer is spaced apart from a/the moisture barrier layer lateral edge along a/the laterally inward direction.

A27. The garment of any of paragraphs A1-A24, wherein a/the one or more base layers includes an/the interior base layer; wherein the anti-leak portion includes a/the moisture barrier layer; and wherein a/the base layer lateral outward edge of the interior base layer is spaced apart from a/the moisture barrier layer lateral edge along a/the laterally outward direction.

A28. The garment of any of paragraphs A1-A27, wherein a/the one or more base layers includes an/the exterior base layer; and wherein a/the base layer lateral outward edge of the exterior base layer is aligned with a/the moisture capture assembly lateral edge.

A29. The garment of any of paragraphs A1-A27, wherein a/the one or more base layers includes an/the exterior base layer; and wherein a/the base layer lateral outward edge of the exterior base layer is spaced apart from a/the moisture capture assembly lateral edge along a/the laterally inward direction.

A30. The garment of any of paragraphs A1-A27, wherein a/the one or more base layers includes an/the exterior base layer; and wherein a/the base layer lateral outward edge of the exterior base layer is spaced apart from a/the moisture capture assembly lateral edge along a/the laterally outward direction.

A31. The garment of any of paragraphs A1-A30, wherein a/the one or more base layers includes an/the exterior base layer; wherein the anti-leak portion includes a/the moisture barrier layer; and wherein the exterior base layer underlies at least a portion of the moisture barrier layer within one or both of a/the moisture capture assembly peripheral region and a/the moisture capture assembly central region.

A32. The garment of any of paragraphs A1-A31, wherein a/the one or more base layers includes an/the exterior base layer; wherein the anti-leak portion includes a/the moisture barrier layer; and wherein a/the base layer lateral outward edge of the exterior base layer is aligned with a/the moisture barrier layer lateral edge.

A33. The garment of any of paragraphs A1-A31, wherein a/the one or more base layers includes an/the exterior base layer; wherein the anti-leak portion includes a/the moisture barrier layer; and wherein a/the base layer lateral outward edge of the exterior base layer is spaced apart from a/the moisture barrier layer lateral edge along a/the laterally inward direction.

A34. The garment of any of paragraphs A1-A31, wherein a/the one or more base layers includes an/the exterior base layer; wherein the anti-leak portion includes a/the moisture barrier layer; and wherein a/the base layer lateral outward edge of the exterior base layer is spaced apart from a/the moisture barrier layer lateral edge along a/the laterally outward direction.

A35. The garment of any of paragraphs A1-A34, wherein each lateral region bond of a/the pair of lateral region bonds joins the moisture capture assembly to each of an/the interior base layer and an/the exterior base layer.

A36. The garment of any of paragraphs A1-A34, wherein each lateral region bond of a/the pair of lateral region bonds joins the moisture capture assembly to only one of an/the interior base layer or an/the exterior base layer.

A37. The garment of any of paragraphs A1-A36, wherein one or both of an/the interior base layer and an/the exterior base layer extends within a/the crotch region and terminates at, or proximal to, each lateral region bond of a/the pair of lateral region bonds.

A38. The garment of any of paragraphs A1-A37, wherein an/the anterior region bond joins the moisture capture assembly to each of an/the interior base layer and an/the exterior base layer.

A39. The garment of any of paragraphs A1-A37, wherein an/the anterior region bond joins the moisture capture assembly to only one of an/the interior base layer or an/the exterior base layer.

A40. The garment of any of paragraphs A1-A39, wherein an/the anterior region bond joins the moisture capture assembly to an/the interior base layer; and wherein an/the exterior base layer is uncoupled from the moisture capture assembly proximal to the anterior region bond.

A40.1. The garment of paragraph A40, wherein the anterior region bond does not join the moisture capture assembly to the exterior base layer.

A41. The garment of any of paragraphs A1-A40.1, wherein one or both of an/the interior base layer and an/the exterior base layer extends within a/the crotch region and away from the crotch region along a laterally anterior direction.

A42. The garment of any of paragraphs A1-A41, wherein one or both of a/the interior base layer and an/the exterior base layer extends within a/the crotch region and terminates at, or proximal to, an/the anterior region bond.

A43. The garment of any of paragraphs A1-A42, wherein a/the posterior region bond joins the moisture capture assembly to each of an/the interior base layer and an/the exterior base layer.

A44. The garment of any of paragraphs A1-A42, wherein a/the posterior region bond joins the moisture capture assembly to only one of an/the interior base layer or an/the exterior base layer.

A45. The garment of any of paragraphs A1-A44, wherein one or both of an/the interior base layer and an/the exterior base layer extends within a/the crotch region and away from the crotch region along a laterally posterior direction.

A46. The garment of any of paragraphs A1-A45, wherein one or both of a/the interior base layer and an/the exterior base layer extends within a/the crotch region and terminates at, or proximal to, a/the posterior region bond.

A47. The garment of any of paragraphs A1-A46, wherein the garment base includes one or more connected base layers; wherein each connected base layer of the one or more connected base layers:
(i) does not extend within a/the crotch region; and
(ii) is joined to the moisture capture assembly by one or both of an/the anterior region bond and a/the posterior region bond.

A47.1. The garment of paragraph A47, wherein the one or more connected base layers includes an interior connected base layer that extends immediately adjacent to the interior base layer at one or both of the anterior region bond and the posterior region bond.

A47.1.1. The garment of paragraph A47.1, wherein the interior connected base layer directly engages the interior base layer.

A47.2. The garment of any of paragraphs A47-A47.1.1, wherein the one or more connected base layers includes an exterior connected base layer that extends immediately adjacent to the exterior base layer at one or both of the anterior region bond and the posterior region bond.

A47.2.1. The garment of paragraph A47.2, wherein the exterior connected base layer directly engages the exterior base layer.

A47.3. The garment of any of paragraphs A47-A47.2.1, wherein each connected base layer of the one or more connected base layers at least partially conceals one or both of an/the anterior region bond and a/the posterior region bond.

A48. The garment of any of paragraphs A1-A47.3, wherein a/the posterior region bond further joins the moisture capture assembly, the interior base layer, and the exterior base layer to a pair of base panels of a/the plurality of base panels.

A48.1. The garment of paragraph A48, wherein the pair of base panels extends away from the crotch region.

A48.2. The garment of any of paragraphs A48-A48.1, wherein the pair of base panels at least partially conceal the posterior region bond.

A49. The garment of any of paragraphs A1-A48.2, wherein the one or more bonds includes a pair of edge binding strip bonds; and wherein each edge binding strip bond of the pair of edge binding strip bonds includes stitching that passes through each of a/the interior base layer, the moisture capture assembly, a/the exterior base layer, and a respective edge binding strip of the pair of edge binding strips to join the respective edge binding strip to the garment base.

A49.1. The garment of paragraph A49, wherein each edge binding strip bond of the pair of edge binding strip bonds is aligned with and/or at least partially overlaps a respective lateral region bond of a/the pair of lateral region bonds.

A49.2. The garment of paragraph A49, wherein each edge binding strip bond of the pair of edge binding strip bonds is laterally offset relative to a/the respective lateral region bond of a/the pair of lateral region bonds along a/the laterally inward direction.

A49.3. The garment of paragraph A49, wherein each edge binding strip bond of the pair of edge binding strip bonds is laterally offset relative to a/the respective lateral region bond of a/the pair of lateral region bonds along a/the laterally outward direction.

A49.4. The garment of any of paragraphs A49-A49.3, wherein each edge binding strip bond of the pair of edge binding strip bonds includes stitching that passes through a respective elastic strip of a/the pair of edge binding strips.

A50. The garment of any of paragraphs A1-A49.4, wherein one or more of the garment base, a/the one or more base layers, an/the interior base layer, and an/the exterior base layer is at least partially formed of one or more of a natural fiber, cotton, a synthetic fiber, polyester, nylon, Spandex™ fabric, and combinations thereof.

A51. The garment of any of paragraphs A1-A50, wherein one or more of the moisture capture assembly, a/the moisture retention portion, a/the first moisture retention layer, a/the second moisture retention layer, a/the wicking layer, and a/the moisture barrier layer is at least partially formed of one or more of a natural fiber, cotton, a synthetic fiber, polyester, nylon, Spandex™ fabric, and combinations thereof.

A52. The garment of any of paragraphs A1-A51, wherein the garment is an article of swimwear.

A52.1. The garment of paragraph A52, wherein the garment is one or more of a swimsuit, a one-piece swimsuit, a swimsuit bottom, and a bikini bottom.

A53. The garment of any of paragraphs A1-A52.1, wherein the garment includes a torso region configured to overlie at least a portion of the wearer's torso when the wearer wears the garment.

A54. The garment of any of paragraphs A1-A53, wherein the garment includes one or more shoulder straps configured to be worn over the wearer's shoulders when the wearer wears the garment; and optionally wherein a/the torso region includes the one or more shoulder straps.

A55. The garment of any of paragraphs A1-A54, wherein the garment includes one or more breast cups configured to overlie and/or support the wearer's breasts when the wearer wears the garment; and optionally wherein a/the torso region includes the one or more breast cups.

A56. The garment of any of paragraphs A1-A55, wherein the garment is an undergarment.

A57. The garment of any of paragraphs A1-A56, wherein the garment is an outerwear garment.

A58. The garment of any of paragraphs A1-A57, wherein the garment is a short.

A59. The garment of any of paragraphs A1-A58, wherein the garment is an activewear garment.

A60. The garment of any of paragraphs A1-A59, wherein the garment is configured to be washed and re-worn numerous times.

B1. A garment configured to be worn by a wearer and to be washed and re-worn numerous times, the garment comprising:
one or more bonds formed within a joined region of the garment;
a garment base comprising at least one interior base layer and at least one exterior base layer; and
a moisture capture assembly joined to the garment base within at least the joined region, wherein the moisture capture assembly has an assembly interior side that faces the wearer when the garment is worn by the wearer, an assembly exterior side that faces away from the wearer when the garment is worn by the wearer, a moisture capture assembly anterior edge, a moisture capture assembly posterior edge opposite the moisture capture assembly anterior edge, and moisture capture assembly lateral edges that extend between the moisture capture assembly posterior edge and the moisture capture assembly anterior edge, wherein the moisture capture assembly is positioned with a crotch region of the garment, and wherein the moisture capture assembly comprises:
  a moisture retention portion configured to absorb and retain moisture from the wearer; and
  an anti-leak portion configured to restrict moisture from exiting the moisture retention portion;
  wherein the one or more bonds comprises an anterior region bond that joins the moisture capture assembly to the at least one interior base layer along the moisture capture assembly anterior edge; and
  wherein the moisture capture assembly is not joined to the at least one exterior base layer along the moisture capture assembly anterior edge.

B2. The garment of paragraph B1, wherein the anterior region bond comprises a stitching seam.

B3. The garment of any of paragraphs B1-B2, wherein the one or more bonds comprises a posterior region bond that joins the moisture capture assembly to the at least one interior base layer and to the at least one exterior base layer along the moisture capture assembly anterior edge.

B3.1. The garment of paragraph B3, wherein the posterior region bond comprises a stitching seam.

B3.2. The garment of any of paragraphs B3-B3.1, wherein the one or more bonds comprises lateral region bonds that join the moisture capture assembly lateral edges to the at least one interior base layer and to the at least one exterior base layer.

B3.2.1. The garment of paragraph B3.2, wherein the lateral region bonds each comprise a stitching seam.

B3.2.2. The garment of any of paragraphs B3.2-B3.2.1; wherein the garment defines a pair of leg openings and further comprises a pair of edge binding strips that extend around the leg openings;
  wherein each edge binding strip extends around a respective moisture capture assembly lateral edge from the assembly interior side to the assembly exterior side;
  wherein the one or more bonds comprises a pair of edge binding strip bonds that join the pair of edge binding strips to the moisture capture assembly along the moisture capture assembly lateral edges.

B3.2.2.1. The garment of paragraph B3.2.2, wherein the edge binding strip bonds each comprise a stitching seam.

B3.2.2.2. The garment of any of paragraphs B3.2.2-B3.2.2.1, further comprising a pair of elastic strips extending around the leg openings, wherein each edge binding strip at least substantially encloses a respective elastic strip of the pair of elastic strips.

B6.3.2.2.2.1. The garment of paragraph B3.2.2.2, wherein an exterior base layer of the at least one exterior base layer extends between each elastic strip and the moisture capture assembly.

B4. The garment of any of paragraphs B1-B3.2.2.2.1, wherein the anti-leak portion comprises a moisture barrier layer that is operatively coupled to the moisture retention portion.

B5. The garment of any of paragraphs B1-B4,
  wherein the at least one interior base layer comprises an interior connected base layer and the at least one exterior base layer comprises an exterior connected base layer;
  wherein the interior connected base layer and the exterior connected base layer are joined to the moisture capture assembly along the moisture capture assembly posterior edge on opposing sides of the moisture capture assembly and extend away from the moisture capture assembly.

B5.1. The garment of paragraph B5,
  wherein the at least one interior base layer further comprises a second interior base layer that is joined to the moisture capture assembly along the moisture capture assembly posterior edge between the moisture capture assembly and the interior connected base layer; and
  wherein the at least one exterior base layer further comprises a second exterior base layer that is joined to the moisture capture assembly along the moisture capture assembly posterior edge opposite the second interior base layer and between the moisture capture assembly and the exterior connected base layer.

B5.1.1. The garment of paragraph B5.1, wherein the second interior base layer is the interior base layer that is joined to the moisture capture assembly along the moisture capture assembly anterior edge, and wherein the second exterior base layer is the exterior base layer that is not joined to the moisture capture assembly along the moisture capture assembly anterior edge.

B6. The garment of any of paragraphs B1-B5.1.1, wherein the one or more bonds each comprises one or more stitching seams.

B7. The garment of any of paragraphs B1-B6, wherein the garment is an article of swimwear.

B8. The garment of any of paragraphs B1-B7, further comprising the subject matter of any of paragraphs A1-A60.

B9. A method of manufacturing the garment of any of paragraphs B1-B8, the method comprising:
  joining, with the one or more bonds, the moisture capture assembly to the garment base.

C1. A garment configured to be worn by a wearer and to be washed and re-worn numerous times, the garment comprising:
  stitching seams formed within a joined region of the garment;
  a garment base comprising at least one interior base layer and at least one exterior base layer, wherein the garment base defines leg openings; and
  a moisture capture assembly joined to the garment base within at least the joined region, wherein the moisture capture assembly has an assembly interior side that faces the wearer when the garment is worn by the wearer, an assembly exterior side that faces away from the wearer when the garment is worn by the wearer, a moisture capture assembly anterior edge, a moisture capture assembly posterior edge opposite the moisture capture assembly anterior edge, and moisture capture assembly lateral edges that extend between the moisture capture assembly posterior edge and the moisture capture assembly anterior edge, wherein the moisture capture assembly is positioned with a crotch region of the garment, and wherein the moisture capture assembly comprises:
    a moisture retention portion configured to absorb and retain moisture from the wearer; and
    an anti-leak portion configured to restrict moisture from exiting the moisture retention portion;
  a pair of edge binding strips that extend around the leg openings;
  a pair of elastic strips extending around the leg openings, wherein each edge binding strip at least substantially encloses a respective elastic strip of the pair of elastic strips;
  wherein the stitching seams comprise:
    an anterior region stitching seam that joins the moisture capture assembly to the at least one interior base layer along the moisture capture assembly anterior edge;
    a posterior region stitching seam that joins the moisture capture assembly to the at least one interior base layer and to the at least one exterior base layer along the moisture capture assembly anterior edge;

lateral region stitching seams that join the moisture capture assembly lateral edges to the at least one interior base layer and to the at least one exterior base layer;

a pair of edge binding strip stitching seams that join the pair of edge binding strips to the moisture capture assembly along the moisture capture assembly lateral edges;

wherein the moisture capture assembly is not joined to the at least one exterior base layer along the moisture capture assembly anterior edge;

wherein each edge binding strip extends around a respective moisture capture assembly lateral edge from the assembly interior side to the assembly exterior side;

wherein an exterior base layer of the at least one exterior base layer extends between each elastic strip and the moisture capture assembly;

wherein the at least one interior base layer comprises an interior connected base layer and the at least one exterior base layer comprises an exterior connected base layer;

wherein the interior connected base layer and the exterior connected base layer are joined to the moisture capture assembly along the moisture capture assembly posterior edge on opposing sides of the moisture capture assembly and extend away from the moisture capture assembly;

wherein the at least one interior base layer further comprises a second interior base layer that is joined to the moisture capture assembly along the moisture capture assembly posterior edge between the moisture capture assembly and the interior connected base layer;

wherein the at least one exterior base layer further comprises a second exterior base layer that is joined to the moisture capture assembly along the moisture capture assembly posterior edge opposite the second interior base layer and between the moisture capture assembly and the exterior connected base layer;

wherein the second interior base layer is the interior base layer that is joined to the moisture capture assembly along the moisture capture assembly anterior edge; and wherein the second exterior base layer is the exterior base layer that is not joined to the moisture capture assembly along the moisture capture assembly anterior edge.

C2. The garment of paragraph C1, further comprising the subject matter of any of paragraphs A1-B7.

C3. A method of manufacturing the garment of any of paragraphs C1-C2, the method comprising, joining, with the stitching seams, the moisture capture assembly to the garment base.

D1. A method of manufacturing a garment configured to be worn by a wearer, the method comprising:

joining a moisture capture assembly to a garment base of the garment within at least a joined region of the garment;

wherein the moisture capture assembly includes a moisture retention portion configured to absorb and retain moisture from the wearer and an anti-leak portion configured to restrict moisture from exiting the moisture retention portion; and wherein the joining the moisture capture assembly to the garment base includes forming one or more bonds, optionally one or more stitching seams, within the joined region.

D2. The method of paragraph D1, wherein the garment is the garment of any of paragraphs A1-C2.

D3. The method of any of paragraphs D1-D2, wherein the joining the moisture capture assembly to the garment base includes joining two or more layers of the moisture capture assembly to one another; optionally wherein the two or more layers of the moisture capture assembly include two or more of the moisture retention portion, the anti-leak portion, a/the one or more moisture retention layers, a/the first moisture retention layer, a/the second moisture retention layer, a/the wicking layer, and a/the moisture barrier layer.

D4. The method of any of paragraphs D1-D3, wherein the joining the moisture capture assembly to the garment base includes, prior to the forming the one or more bonds, positioning a/the two or more layers of the moisture capture assembly between an/the interior base layer and an/the exterior base layer.

D5. The method of any of paragraphs D1-D4, wherein the forming the one or more bonds includes forming a/the pair of lateral region bonds.

D5.1. The method of paragraph D5, wherein the moisture capture assembly includes a/the moisture capture assembly peripheral region that includes a/the pair of moisture capture assembly lateral edges; and wherein the forming the pair of lateral region bonds includes forming each lateral region bond of the pair of lateral region bonds at a respective moisture capture assembly lateral edge of the pair of moisture capture assembly lateral edges.

D6. The method of any of paragraphs D1-D5.1, wherein the forming the one or more bonds includes forming a/the anterior region bond.

D6.1. The method of paragraph D6, wherein the moisture capture assembly includes a/the moisture capture assembly peripheral region that includes a/the moisture capture assembly anterior edge; and wherein the forming the anterior region bond includes forming the anterior region bond at the moisture capture assembly anterior edge.

D7. The method of any of paragraphs D1-D6.1, wherein the forming the one or more bonds includes forming a/the posterior region bond.

D7.1. The method of paragraph D7, wherein the moisture capture assembly includes a/the moisture capture assembly peripheral region that includes a/the moisture capture assembly posterior edge; and wherein the forming the posterior region bond includes forming the posterior region bond at the moisture capture assembly posterior edge.

D8. The method of any of paragraphs D1-D7.1, further comprising, prior to the joining the moisture capture assembly to the garment base, preparing the moisture capture assembly.

D8.1. The method of paragraph D8, wherein the preparing the moisture capture assembly includes shaping the moisture capture assembly.

D8.1.1. The method of paragraph D8.1, wherein the shaping the moisture capture assembly includes cutting the moisture capture assembly to a desired shape.

D8.1.2. The method of any of paragraphs D8.1-D8.1.1, wherein the shaping the moisture capture assembly includes die cutting.

D9. The method of any of paragraphs D1-D8.1.2, wherein the garment defines a/the pair of garment lateral edges; wherein the garment comprises a/the pair of edge binding strips, and wherein the method further comprises joining each edge binding strip of the pair of edge binding strips to a respective garment lateral edge of the pair of garment lateral edges.

D9.1. The method of paragraph D9, wherein the joining each edge binding strip to the respective garment lateral edge is performed subsequent to the joining the moisture capture assembly to the garment base.

D9.2. The method of any of paragraphs D9-D9.1, wherein the joining each edge binding strip to the respective garment lateral edge includes forming a/the pair of edge binding strip bonds.

D9.3. The method of any of paragraphs D9-D9.2, wherein the joining each edge binding strip to the respective garment lateral edge includes joining a/the pair of elastic strips to the pair of garment lateral edges, optionally with a/the pair of edge binding strip bonds.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the term "and/or" placed between a first entity and a second entity means one of (1) the first entity, (2) the second entity, and (3) the first entity and the second entity. Multiple entries listed with "and/or" should be construed in the same manner, i.e., "one or more" of the entities so conjoined. Other entities optionally may be present other than the entities specifically identified by the "and/or" clause, whether related or unrelated to those entities specifically identified. Thus, as a non-limiting example, a reference to "A and/or B," when used in conjunction with open-ended language such as "comprising," may refer, in one example, to A only (optionally including entities other than B); in another example, to B only (optionally including entities other than A); in yet another example, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entities in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C," and "A, B, and/or C" may mean A alone, B alone, C alone, A and B together, A and C together, B and C together, A, B, and C together, and optionally any of the above in combination with at least one other entity.

As used herein, the phrase "at least substantially," when modifying a degree or relationship, includes not only the recited "substantial" degree or relationship, but also the full extent of the recited degree or relationship. A substantial amount of a recited degree or relationship may include at least 75% of the recited degree or relationship. For example, a first component that extends at least substantially around a second component includes a first component that extends around at least 75% of a circumference of the second component and also includes a first component that extends fully circumferentially around the second component.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

The various disclosed elements of apparatuses disclosed herein are not required to all apparatuses according to the present disclosure, and the present disclosure includes all novel and non-obvious combinations and subcombinations of the various elements disclosed herein. Moreover, one or more of the various elements disclosed herein may define independent inventive subject matter that is separate and apart from the whole of a disclosed apparatus. Accordingly, such inventive subject matter is not required to be associated with the specific apparatuses that are expressly disclosed herein, and such inventive subject matter may find utility in apparatuses and/or methods that are not expressly disclosed herein.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, when the disclosure or subsequently filed claims recite "a" or "a first" element or the equivalent thereof, such disclosure and/or claims should be understood to include incorporation of one or more such elements, neither requiring nor excluding two or more such elements.

The invention claimed is:

1. A garment configured to be worn by a wearer and to be washed and re-worn numerous times, the garment comprising:
   one or more bonds formed within a joined region of the garment;
   a garment base comprising at least one interior base layer and at least one exterior base layer; and a moisture capture assembly joined to the garment base within at least the joined region, wherein the moisture capture assembly has an assembly interior side that faces the wearer when the garment is worn by the wearer, an assembly exterior side that faces away from the wearer when the garment is worn by the wearer, a moisture capture assembly anterior edge, a moisture capture assembly posterior edge opposite the moisture capture assembly anterior edge, and moisture capture assembly lateral edges that extend between the moisture capture assembly posterior edge and the moisture capture assembly anterior edge, wherein the moisture capture assembly is positioned with a crotch region of the garment, and wherein the moisture capture assembly comprises:
  a moisture retention portion configured to absorb and retain moisture from the wearer; and
  an anti-leak portion configured to restrict moisture from exiting the moisture retention portion;
wherein the one or more bonds comprises an anterior region bond that joins the moisture capture assembly to the at least one interior base layer along the moisture capture assembly anterior edge; and
wherein the moisture capture assembly is not joined to the at least one exterior base layer along the moisture capture assembly anterior edge.

2. The garment of claim 1, wherein the anterior region bond comprises a stitching seam.

3. The garment of claim 1, wherein the one or more bonds comprises a posterior region bond that joins the moisture capture assembly to the at least one interior base layer and to the at least one exterior base layer along the moisture capture assembly anterior edge.

4. The garment of claim 3, wherein the anterior region bond and the posterior region bond each comprise a stitching seam.

5. The garment of claim 3, wherein the one or more bonds comprises lateral region bonds that join the moisture capture assembly lateral edges to the at least one interior base layer and to the at least one exterior base layer.

6. The garment of claim 5, wherein the anterior region bond, the posterior region bond, and the lateral region bonds each comprise a stitching seam.

7. The garment of claim 5;
wherein the garment defines a pair of leg openings and further comprises a pair of edge binding strips that extend around the leg openings;
wherein each edge binding strip extends around a respective moisture capture assembly lateral edge from the assembly interior side to the assembly exterior side;
wherein the one or more bonds comprises a pair of edge binding strip bonds that join the pair of edge binding strips to the moisture capture assembly along the moisture capture assembly lateral edges.

8. The garment of claim 7, wherein the anterior region bond, the posterior region bond, the lateral region bonds, and the edge binding strip bonds each comprise a stitching seam.

9. The garment of claim 7, further comprising a pair of elastic strips extending around the leg openings, wherein each edge binding strip at least substantially encloses a respective elastic strip of the pair of elastic strips.

10. The garment of claim 9, wherein an exterior base layer of the at least one exterior base layer extends between each elastic strip and the moisture capture assembly.

11. The garment of claim 1, wherein the anti-leak portion comprises a moisture barrier layer that is operatively coupled to the moisture retention portion.

12. The garment of claim 1,
wherein the at least one interior base layer comprises an interior connected base layer and the at least one exterior base layer comprises an exterior connected base layer;
wherein the interior connected base layer and the exterior connected base layer are joined to the moisture capture assembly along the moisture capture assembly posterior edge on opposing sides of the moisture capture assembly and extend away from the moisture capture assembly.

13. The garment of claim 12,
wherein the at least one interior base layer further comprises a second interior base layer that is joined to the moisture capture assembly along the moisture capture assembly posterior edge between the moisture capture assembly and the interior connected base layer; and
wherein the at least one exterior base layer further comprises a second exterior base layer that is joined to the moisture capture assembly along the moisture capture assembly posterior edge opposite the second interior base layer and between the moisture capture assembly and the exterior connected base layer.

14. The garment of claim 13, wherein the second interior base layer is the interior base layer that is joined to the moisture capture assembly along the moisture capture assembly anterior edge, and wherein the second exterior base layer is the exterior base layer that is not joined to the moisture capture assembly along the moisture capture assembly anterior edge.

15. The garment of claim 1, wherein the one or more bonds each comprises one or more stitching seams.

16. The garment of claim 1, wherein the garment is an article of swimwear.

17. A method of manufacturing the garment of claim 1, the method comprising:
joining, with the one or more bonds, the moisture capture assembly to the garment base.

18. A garment configured to be worn by a wearer and to be washed and re-worn numerous times, the garment comprising:
stitching seams formed within a joined region of the garment;
a garment base comprising at least one interior base layer and at least one exterior base layer, wherein the garment base defines leg openings; and
  a moisture capture assembly joined to the garment base within at least the joined region, wherein the moisture capture assembly has an assembly interior side that faces the wearer when the garment is worn by the wearer, an assembly exterior side that faces away from the wearer when the garment is worn by the wearer, a moisture capture assembly anterior edge, a moisture capture assembly posterior edge opposite the moisture capture assembly anterior edge, and moisture capture assembly lateral edges that extend between the moisture capture assembly posterior edge and the moisture capture assembly anterior edge, wherein the moisture capture assembly is positioned with a crotch region of the garment, and wherein the moisture capture assembly comprises:
    a moisture retention portion configured to absorb and retain moisture from the wearer; and
    an anti-leak portion configured to restrict moisture from exiting the moisture retention portion;
a pair of edge binding strips that extend around the leg openings;

a pair of elastic strips extending around the leg openings, wherein each edge binding strip at least substantially encloses a respective elastic strip of the pair of elastic strips;

wherein the stitching seams comprise:
- an anterior region stitching seam that joins the moisture capture assembly to the at least one interior base layer along the moisture capture assembly anterior edge;
- a posterior region stitching seam that joins the moisture capture assembly to the at least one interior base layer and to the at least one exterior base layer along the moisture capture assembly anterior edge;
- lateral region stitching seams that join the moisture capture assembly lateral edges to the at least one interior base layer and to the at least one exterior base layer;
- a pair of edge binding strip stitching seams that join the pair of edge binding strips to the moisture capture assembly along the moisture capture assembly lateral edges;

wherein the moisture capture assembly is not joined to the at least one exterior base layer along the moisture capture assembly anterior edge;

wherein each edge binding strip extends around a respective moisture capture assembly lateral edge from the assembly interior side to the assembly exterior side;

wherein an exterior base layer of the at least one exterior base layer extends between each elastic strip and the moisture capture assembly;

wherein the at least one interior base layer comprises an interior connected base layer and the at least one exterior base layer comprises an exterior connected base layer;

wherein the interior connected base layer and the exterior connected base layer are joined to the moisture capture assembly along the moisture capture assembly posterior edge on opposing sides of the moisture capture assembly and extend away from the moisture capture assembly;

wherein the at least one interior base layer further comprises a second interior base layer that is joined to the moisture capture assembly along the moisture capture assembly posterior edge between the moisture capture assembly and the interior connected base layer;

wherein the at least one exterior base layer further comprises a second exterior base layer that is joined to the moisture capture assembly along the moisture capture assembly posterior edge opposite the second interior base layer and between the moisture capture assembly and the exterior connected base layer;

wherein the second interior base layer is the interior base layer that is joined to the moisture capture assembly along the moisture capture assembly anterior edge; and wherein the second exterior base layer is the exterior base layer that is not joined to the moisture capture assembly along the moisture capture assembly anterior edge.

19. A method of manufacturing the garment of claim 18, the method comprising:
joining, with the stitching seams, the moisture capture assembly to the garment base.

* * * * *

UNITED STATES PATENT AND TRADEMARK OFFICE
CERTIFICATE OF CORRECTION

| | |
|---|---|
| PATENT NO. | : 11,701,267 B2 |
| APPLICATION NO. | : 17/718127 |
| DATED | : July 18, 2023 |
| INVENTOR(S) | : Christina Greco et al. |

It is certified that error appears in the above-identified patent and that said Letters Patent is hereby corrected as shown below:

In the Specification

At Column 27, Line 22, "along the moisture capture assembly anterior edge" should read "along the moisture capture assembly posterior edge"

In the Claims

In Claim 3, Column 33, Line 33, "capture assembly anterior edge" should read "capture assembly posterior edge"

In Claim 18, Column 35, Line 13, "the moisture capture assembly anterior edge" should read "the moisture capture assembly posterior edge"

Signed and Sealed this
Fifteenth Day of October, 2024

Katherine Kelly Vidal
*Director of the United States Patent and Trademark Office*